United States Patent [19]

Molino et al.

[11] Patent Number: 5,162,336

[45] Date of Patent: Nov. 10, 1992

[54] TETRAHYDRO-PYRIDO-INDOLES AS CHOLECYSTOKININ AND GASTRIN ANTAGONISTS

[75] Inventors: Bruce F. Molino, Hatfield; Paul R. Darkes, Lansdale; William R. Ewing, King of Prussia, all of Pa.

[73] Assignee: Rhône-Poulenc Rorer Pharmaceuticals Inc., Collegeville, Pa.

[21] Appl. No.: 573,514

[22] Filed: Aug. 24, 1990

Related U.S. Application Data

[63] Continuation-in-part of Ser. No. 542,495, Jun. 21, 1990, abandoned.

[51] Int. Cl.$^5$ .................... C07D 471/04; A61K 31/44
[52] U.S. Cl. ....................................... 514/292; 546/85; 546/86; 546/87
[58] Field of Search ................ 546/85, 86, 87; 514/292

[56] References Cited

U.S. PATENT DOCUMENTS

| | | | |
|---|---|---|---|
| 4,559,339 | 12/1985 | Bock et al. | 514/219 |
| 4,757,068 | 7/1988 | Parsons | 514/213 |
| 4,847,248 | 7/1989 | Freidinger et al. | 514/214 |

FOREIGN PATENT DOCUMENTS

| | | | |
|---|---|---|---|
| 166355 | 2/1986 | European Pat. Off. | 548/491 |
| 250148 | 12/1987 | European Pat. Off. | 548/491 |
| 304223 | 2/1989 | European Pat. Off. | 546/86 |
| 405537 | 1/1991 | European Pat. Off. | 548/491 |

OTHER PUBLICATIONS

Coutts, R. T. et al., Heterocycles 22(1), 131-142 (1984) "Some 3-Carboxamides of β-Carboline and Tetrahydro-β-Carboline".

Cain, M., et al., J. Med. Chem. 25, 1081 (1982) "β-Carbolines: Synthesis and Neurochemical and Pharmacological Actions on Brain Benzodiazepine Receptors".

Itonaga, M., et al., Japan. J. Pharmacol. 46, 319-324 (1988) "Cholecystokinin Antagonism by β-Carboline Esters in the Central Nervous System in Mice".

Hahne, W. F., et al., Proc. Natl. Acad. Sci. USA 78(1), 6304-6308 (1981) "Proglumide and benzotript: Members of a Different Class of Cholecystokinin Receptor Antagonists".

Evans, B. E., et al., J. Med. Chem. 1988, 31, 2235-2246 "Methods for Drug Discovery: Development of Potent, Selective, Orally Effective Cholecystokinin Antagonists".

Parsons, W. H., et al., J. Med. Chem. 1989, 32, 1681-1685 "Cholecystokinin Antagonists, Synthesis and Biological Evaluation of 3-Substituted Benzolactams".

Primary Examiner—Alan L. Rotman
Attorney, Agent, or Firm—Paul R. Darkes; Martin F. Savitzky

[57] ABSTRACT

Disclosed are tetrahydro-pyrido-indoles having the general formula

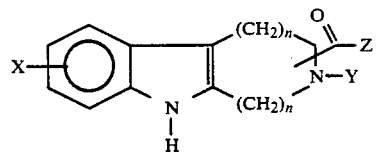

which are antagonists towards the neuropeptides cholexystokinin and gastrin processing valuable activities for the treatment of cholecystokinin or gastrin-related disorders of the gastrointestinal, central nervous and appetite regulatory systems and their pharmaceutical compositions and processes for their preparation.

20 Claims, No Drawings

TETRAHYDRO-PYRIDO-INDOLES AS CHOLECYSTOKINEN AND GASTRIN ANTAGONISTS

This application is a continuation-in-part application of application Ser. No. 07/542,495 filed on Jun. 21, 1990, now abandoned.

BACKGROUND OF THE INVENTION

1. Field of the Invention

This invention relates to certain compounds having antagonistic activity towards the neuropeptides cholecystokinin (hereinafter CCK) and gastrin.

CCK and gastrin are peptides, endogenous in human and other species, which regulate biological functions in tissues in the GI tract and central nervous systems (CNS). Gastrin and CCK regulate biological activity by acting as autocrine, parocrine, endocrine or neuromodulatory agents.

The first and principal form of gastrin isolated was the 17 amino acid residue peptide, G-17 or little gastrin. The second major molecular form of gastrin is the 34 amino acid residue peptide, G-34 or big gastrin. G-34 is considered the proform of G-17, but both forms of gastrin are biologically active and nearly equipotent. The smallest residue possessing biological activity is G-4 which is the final 4 amino acids at the carboxyl terminal. Sulfation of the tyrosine residue (6-amino acids from the C-terminal) is not necessary for expression of the bioactivity of gastrins.

The major physiologic action of gastrin is the stimulation of acid secretion from the stomach. Gastrin stimulates acid secretion by at least three separate actions: direct stimulation of parietal cell activity; potentiating interaction with histamine, a paracrine stimulus; and, quantitatively, by release of histamine.

Gastrin is a trophic hormone for gastric, fundic and intestinal mucosa and for the pancreas. Gastrin directly stimulates those biochemical processes, DNA and RNA synthesis, that are involved in tissue growth.

Gastrin also stimulates pepsin secretion and increases gastric mucosal blood flow. It causes electrolyte and water secretion by the stomach, pancreas, liver, and Brunner's glands.

Other possible actions of gastrin may involve the regulation of lower esophageal sphincter contraction and other smooth muscle contractions (motility) in the GI tract.

CCK is a linear amino acid polypeptide that occurs in several bioactive molecular forms: CCK-8, CCK-22, CCK-33, CCK-39 and CCK-58 are the major forms which have been reported. All of the CCK variants require the sulfation of the tyrosine residue at position 7, counting from the C-terminal, for the full expression of their biologic activity.

The principal physiologic actions of CCK are stimulation of contraction of gallbladder and of pancreatic enzyme secretion. There is evidence which supports a physiological role of CCK in the inhibition of gastric emptying, stimulation of pancreatic growth and release of pancreatic polypeptide.

Other possible actions of CCK include stimulation of insulin, glucagon, somatostatin and peptide YY release, stimulation of hepatic bile flow, intestinal motility, blood flow in the superior mesenteric artery, secretion of pepsinogen from gastric glands, and secretion of bicarbonate from the stomach and duodenum. In contrast to gastrin, CCK relaxes the lower esophageal sphincter.

In the nervous system CCK may act as a neurotransmitter or as a neuromodulator. As such, exogeneous CCK has been shown to effect memory. Also levels of acetylcholine and dopamine have been effected by exogenoeus CCK. CCK has been implicated as well for producing the satiety effect, however, it is not clear if this is regulated by peripheral or central mechanisms.

There is considerable overlap in the biological activities elicited by gastrin and CCK. Therefore, antagonists for gastrin or CCK may also possess activities at the CCK or gastrin receptors.

2. Reported Developments

Four distinct chemical classes of CCK-A (peripheral CCK) receptor antagonists have been reported (see R. M. Freidinger, *Medicinal Research Reviews*, Vol. 9, No. 3, 271-290 (1989)).

(1) Cyclic nucleotides eg. dibutyryl cyclic GMP (see N. Boilos et al., *Am. J. Physiol.* 242, G 161 (1982) and P. Robberecht et al., *Mol. Pharmacol.*, 17, 268 (1982).

(2) Amino acid derivatives, characterized by proglumide, a derivation of glutaramic acid and N-acylated tryptophans, i.e. para-chlorobenzoyl-L-tryptophan (benzotrypt) (see W. F. Hohne et al., *Proc. Natl. Acad. Sci. USA*, 87, 6304 (1981) and R. T. Jensen et al., *Biochem. Biophys. Acta.* 761, 269 (1983); also second generation proglumide analogues typified by Lorglumide and Loxiglumide (F. Makovec et al., *Arzneim-Forsch.*, 37(II), 1265 (1987)). The latter two analogues have considerably better receptor affinity and selectivity.

(3) Peptide and pseudopeptide analogs based on the C-terminal end of CCK, especially analogues of CCK-8, Asp-Tyr($SO_3H$)-Met-Gly-Trp-Met-Asp-Phe-$NH_2$. Some examples are Cbz-Tyr($SO_3H$)-Met-Gly-Trp-Met-Asp-$NH_2$ (M. Spanarkel et al., *J. Biol. Chem.* 258, 6746 (1983)) and Boc-Tyr($SO_3H$)-Met-Gly-D-Trp-Nle-Asp-$OCH_2CH_2Ph$ (M. F. Lignon et al. *J. Biol. Chem.* 262, 7226 (1987)).

(4) Non-peptide structures—the fermentation product, asperlicin (R. S. L. Chang et al., *Science* 230, 177 (1985)) and subsequent medicinal chemistry done on this compound which culminated in the very high CCK-A affinity 1,4-benzodiazepine (MK329) series (B. E. Evans et al., *J. Med. Chem.* 31, 2235-2246, 1988).

Structurally related compounds which retain nanomolar level potency for CCK have recently been reported, e.g. 3-aminobenzolactam (R. S. L. Chang and W. H. Parsons, Eur. Pat. Appl. EP 166,345, 1986, and W. H. Parsons et al., *J. Med. Chem.*, 32, 1681-1685, 1989) and β-carbolines (B. E. Evans, Eur. Pat. Appl. EP 304233, 1988 and M. Itonaga et al , *Japan. J. Pharmacol.*, 46, 319-324, 1988).

Compounds selective for the peripheral gastrin receptor also possess strong affinity for the CCK-B receptor (a CCK receptor located in CNS). Presently there are no known agents which differentiate between the CCK-B receptor and the peripheral gastrin receptor. Compounds selective for gastrin generally fall into two major classes.

(1) Peptide and pseudopeptide analogs based on C-terminal amino acids of CCK or gastrin, especially CCK-4 (Phe-Met-Asp-Phe-$NH_2$). Some examples are the pseudopeptide Boc-Trp-Leu-Ψ($CH_2NH$)-Asp-Phe-$NH_2$ in which the peptide bond between leucine and aspartic acid has been replaced by $CH_2NH$ bond and has the same binding affinity as Boc-Trp-Leu-Asp-Phe- $NH_2$ but has no agonist activity (J. Martinez et al., *J. Med. Chem.*, 28, 1874, 1985).

Other analogues of CCK-4 containing partial retroinverso modifications have been demonstrated to bind strongly to the gastrin receptor and block the effects of gastrin in the rat (in vivo) eg. Boc-Trp-Leu-gAsp-m(R,S)Phe-$NH_2$ (M. Rodriguez et al., *J. Med. Chem.*, 30, 758-763, 1987).

Recently some cyclic cholecystokinin analogues of CCK-8 (Asp-Tyr($SO_3H$)-Met-Gly Trp-Met-Asp-Phe-$NH_2$) eg.

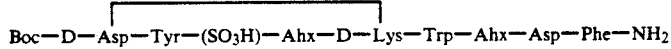

(where Ahx=2-aminohexanoic acid) have demonstrated selectivity for the CCK-B (CNS) receptor relative to CCK-A - (peripheral). (B. Charpentier, et al., *Proc. Natl. Acad. Sci. USA*, 85, 1968-1972, 1988.)

(2) Benzodiazepines - the 3-substituted 1,4-benzodiazepines effective as selective antagonists of CCK-A have been modified synthetically resulting in agents selective for the peripherial gastrin and CCK-B (brain) receptors, such as the Merck compound L-365,260 (V. J. Lotte and R. S. L. Chang, *Env. J. of Pharm.*, 162, 273-280, 1989, also M. G. Bock et al., *J. Med. Chem.*, 32, 16-23, 1989).

Other non-peptide, non-benzodiozepine compounds have been reported (eg. analogs of Virginiamycin M1) to display strong binding affinity selectively for gastrin (relative to CCK-A pancreas) (Y.-K. T. Lam et al., U.S. Pat. No. 4,762,923 (1988)).

Heretofore tetrahydro-pyrido-indoles have not been reported to possess cholecystokinin and/or gastrin antagonists activities.

SUMMARY OF THE INVENTION

The present invention comprises a compound of the

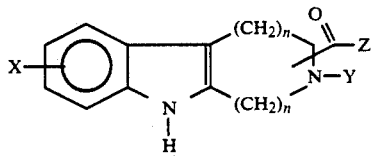

wherein:
X is hydrogen, hydroxy, alkyl, hydroxyalkyl, alkoxy, carboxy, halo, acyl, trihalomethyl, amino, alkyl amino, dialkylamino, acylamino, cyano, alkylcarboxy, formyl, alkylcarbonyl, aryl, substituted aryl, nitro, alkanoyloxy, carbamoyl, carbalkoxy-alkoxy, alkynyl, alkenyl, alkyl sulfinyl, alkyl sulfonyl, alkoxycarbonyl, alkanoyl or alkenoyl;
Y is hydrogen, alkyl, carbobenzoxy, tert-butoxycarbonyl,

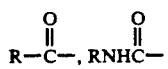

or arylalkyl; Z is $NR_1R_2$, $NHR_3$,

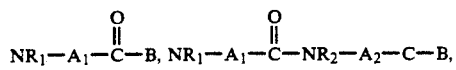

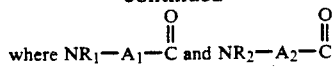

may be derived from natural or synthetic amino acid residues,

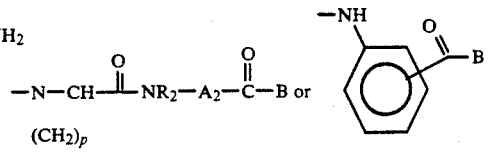

n is 0 to 4;
m is 0 to 3;
wherein:
p is 3, 4 or 5;
R is substituted or unsubstituted phenyl, naphthyl, pyridyl, quinolinyl, isoquinolinyl or indolyl;
$R_1$ is hydrogen, alkyl; substituted or unsubstituted aryl, substituted or unsubstituted heterocyclics;
$R_2$ is hydrogen or alkyl;
$R_3$ is alkyl, aryl, aralkyl, alkylaryl; or substituted aryl, aralkyl or alkylaryl;
$A_1$ and $A_2$ are independently alkylene, arylalkylene, arylalkylalkylene, carboalkoxy-alkylalkylene, carboarylalkoxy alkyl alkylene, carboxyalkylalkylene or alkylthioalkylmethylene;
B is hydroxy, alkoxy, arylalkoxy or $NR_4R_5$, where $R_4$ and $R_5$ are independently hydrogen, alkyl, alkoxy, carboxyalkyl, carboalkoxyalkyl or carboaryloxyalkyl;
or a pharmaceutically acceptable salt thereof.

The present invention also relates to a method of prevention and treatment of disorders of the gastrointestinal, central nervous and appetite-controlling systems of a mammal, such as irritable bowel syndrome, hypergastrinemia, excess pancreatic or gastric secretions, gastrointestinal ulcers, motility and neuroleptic disorders, Parkinson's disease, pain, malignancies of the lower esophagus, stomach, intestines and colon, comprising the administration of a compound described above to said mammal.

The invention also comprises pharmaceutical compositions useful for the prevention and treatment of the aforesaid disorders comprising an aforesaid compound in a pharmaceutically acceptable carrier.

DETAILED DESCRIPTION OF THE INVENTION

As employed above and throughout the disclosure, the following terms, unless otherwise indicated, shall be understood to have the following meanings:

"Alkyl" means, either alone or within the various substitutents, defined hereinbefore, a hydrocarbon having one to about 20 carbon atoms. "Lower alkyl" means alkyl having one to about six carbon atoms, for example, methyl, ethyl, propyl, isopropyl, butyl, isobutyl, amyl and hexyl. Preferred lower alkyl includes methyl, ethyl and propyl.

"Halo" means Cl, Br, I and F.

"Aryl" means a mononuclear and polynuclear aromatic hydrocarbon radical which can be substituted or unsubstituted in one or more positions. Examples of aryl groups include phenyl, naphthyl, anthranyl, phenanthranyl, azulyl and the like which can be substituted with one or more of the substituents. Aryl is preferrably substituted or unsubstituted phenyl or naphthyl. Aryl substituents include hydrogen, alkyl, alkoxy, amino, halo, aryl, aryloxy, carboalkoxy, nitro, dialkylamino, trifluoromethyl, thioalkyl and carbamoyl.

"Aralkyl" means an alkyl group substituted by an aryl radical. The preferred aralkyl groups are lower alkyl groups substituted by phenyl or substituted phenyl. The most preferred aralkyl group is benzyl.

"Acyl" means an organic radical derived from an organic acid by removal of its hydroxy group. Preferred acyl groups are acetyl, propionyl and benzoyl.

"Heterocyclics" denote mononuclear and polynuclear aromatic hydrocarbon groups in which one or more ring carbons have been replaced by a heteroatom such as nitrogen, oxygen, sulfur, phosphorus or a metal. The preferred heterocyclics are the mononuclear aromatic hydrocarbon groups in which one or more of the carbons have been replaced by oxygen or nitrogen. Preferred heterocyclics include oxacyclobutyl, azacyclobutyl, thiacyclobutyl, oxacyclopentyl, azacyclopentyl, thiacyclopentyl, oxacyclohexyl, azacyclohexyl, thiacyclohexyl, pyridyl, furyl, pyrollyl, quinolyl and indolyl. Substution by hydrogen, alkyl, alkoxy, halo or acyl can be either on one or more of the heteroatom or on one or more of the carbon atoms. Substitution on one or more carbon atoms is preferred.

The natural amino acids are bonded to the carbon atom at the α-amino position and include Gly, Ala, Val, Leu, Ile, Phe, Pro, Ser, Thr, Tyr, Asn, Gln, Lys, Arg, Trp, His, Cys, Met, Asp and Glu.

The pharmaceutically acceptable salts of the present invention include those formed from sodium, potassium, calcium, aluminum, lithium, magnesium, zinc, lysine, argininn, procaine, ethylenediamine and piperazine.

Prefered are compounds of the formula wherein
X is hydrogen, hydroxy, alkyl, hydroxyalkyl, alkoxy, carboxy, trihalomethyl;
Y is hydrogen, alkyl, carbobenzoxy, $$R-\overset{O}{\underset{\|}{C}} \text{ or } R-\overset{O}{\underset{\|}{\underset{H}{N-C;}}}$$

Z is NR$_1$R$_2$, NHR$_3$, $$NR_1-A_1-\overset{O}{\underset{\|}{C}}-B, \quad NR_1-A_1-\overset{O}{\underset{\|}{C}}-NR_2-A_2-\overset{O}{\underset{\|}{C}}-B,$$

where NR$_1$—A$_1$—$\overset{O}{\underset{\|}{C}}$ and/or NR$_2$—A$_2$—$\overset{O}{\underset{\|}{C}}$ may be derived from natural or synthetic am acid residues;
n is 1-2;
m is 1-2;
R is phenyl or substituted phenyl wherein said substitution is by hydrogen, alkyl, alkoxy, amino or halo;
R$_1$ is hydrogen, alkyl, phenyl or substituted phenyl;
R$_2$ is hydrogen or alkyl;
R$_3$ is alkyl, substituted or unsubstituted phenyl or naphthyl;
A$_1$ is alkylene or arylalkylene; and
B is hydroxy, alkoxy or aralkoxy.

The more preferred compounds contain the combination of two amino acids.

The most preferred compounds include: N-[(3R)-2-benzoyl-1,2,3,4-tetrahydro-9H-pyrido[3,4-b]indole-3-carboxyl]-L-leucyl-L-aspartic acid amide; N-[(3R)-2-(3-methylphenylcarbamoyl)-1,2,3,4-tetrahydro-9H-pyrido[3,4-b]indole-3-carboxyl]-L-leucyl-L-aspartic acid amide; N-[(3R)-2-phenylcarbamoyl-1,2,3,4-tetrahydro-9H-pyrido-[3,4-b]indole-3-carboxyl]-L-leucyl-L-aspartic acid amide; N-[(3R)-2-(3-methylphenylcarbamoyl)-1,2,3,4-tetrahydro-9H-pyrido[3,4-b]indole-3-carboxyl]-L-aspartic acid dipentyl amide; N-[(3R)-2-(3-methylphenylcarbamoyl)-1,2,3,4-tetrahydro-9H-pyrido[3,4-b]indole-3-carboxyl]-L-leucyl-D-aspartic acid amide; N-[(3S)-2-(3-methylphenylcarbamoyl)1,2,3,4-tetrahydro-9H-pyrido[3,4-b]indole-3-carboxyl]-D-leucyl-L-aspartic acid amide; N-[(3R)-2-(3-methylbenzoyl)-1,2,3,4-tetrahydro-9H-pyrido[3,4-b]indole-3-carboxyl]-L-leucyl-L-aspartic acid amide; N-[(3R)-2-(4-chlorophenylcarbamoyl)-1,2,3,4-tetrahydro-9H-pyrido[3,4-b]indole-3-carboxyl-]-L-leucyl-L-aspartic acid amide; N-[(3R)-2-(3-methylphenylcarbamoyl)-1,2,3,4-tetrahydro-9H-pyrido[3,4-b]indole-3-carboxyl]-D-leucyl-L-aspartic acid amide; N-[(3R)-2-(3,5-dichlorophenylcarbamoyl)-1,2,3,4-tetrahydro- 9H-pyrido[3,4-b]indole-3-carboxyl]-L-leucyl-L-aspartic acid amide; N-[(3R)-2-(3-methoxyphenylcarbamoyl)-1,2,3,4-tetrahydro-9H-pyrido[3,4-b]indole-3-carboxyl]-L-leucyl-L-aspartic acid amide; N-[(3R)-2-(3,4-dichlorophenyl-carbamoyl)-1,2,3,4-tetrahydro-9H-pyrido[3,4-b]indole-3-carboxyl]-L-leucyl-L-aspartic acid amide; and N-[(3R)-2-(1-naphthylcarbamoyl)-1,2,3,4-tetrahydro-9H-pyrido[3,4-b]indole-3-carboxyl]-L-leucyl-L-aspartic acid amide.

The present compounds may be prepared by the following general procedure:

Thus, an amine derivative is coupled to an appropriately substituted 1,2,3,4-tetrahydro-9H-pyrido[3,4-b]indole-3-carboxylic acid. Y represents either the desired substituent for the final product, or may be an appropriate blocking group to prevent cross reaction during the coupling procedure, such blocking groups include, but are not limited to, tertbutoxycarbonyl (BOC), carbobenzoxy (CBZ), and benzyl. The blocking group may then be retained or removed to give the final product, or the deprotected indole may be further derivatized to give the final product. Since the amine derivative may be an amino acid or peptide, or a derivative of an amino acid or peptide, it may also be protected by appropriate blocking groups to prevent cross reaction during the coupling. These protecting groups may likewise be retained or removed by standard methods subsequent to the coupling reaction to give the final product.

The coupling may be effected by methods generally used in peptide synthesis (see for example, M. Bodanszky and A. Bodanszky, *The Practice of Peptide Synthesis.* Springer-Verlag, 1984) or other methods of amide bond formation. One such method involves coupling in the presence of 1-(3-dimethylaminopropyl)-3-ethylcarbodiimide hydrochloride (EDC), in the presence of 1-hydroxybenzotriazole (HBT) and triethylamine in an appropriate solvent such as dimethylformamide (DMF), at room temperature. Another method is that of C. Van der Auwera, et al. (*Int. J. Peptide Protein Res.* 29, 1987, 574–88), whereby the coupling is done in the presence of N,N-bis[2-oxo-3-oxazolinyl]phosphorodiamidic chloride (BOP-Cl), at reduced temperatures in solvents including DMF and tetrahydrofuran (THF). The coupling may also proceed through in situ formation of a mixed anhydride of the carboxylic acid, such as using isopropyl chloroformate in the presence of N-methyl piperidine, followed by reaction with the amine, (see, N. Leo Benoiton, et al., *Int. J. Peptide Protein Res.* 31, 1988, 577–580).

The 1,2,3,4-tetrahydro-9H-pyrido[3,4-b]indole-3-carboxylic acid is available from the corresponding tryptophan, or derivative of tryptophan.

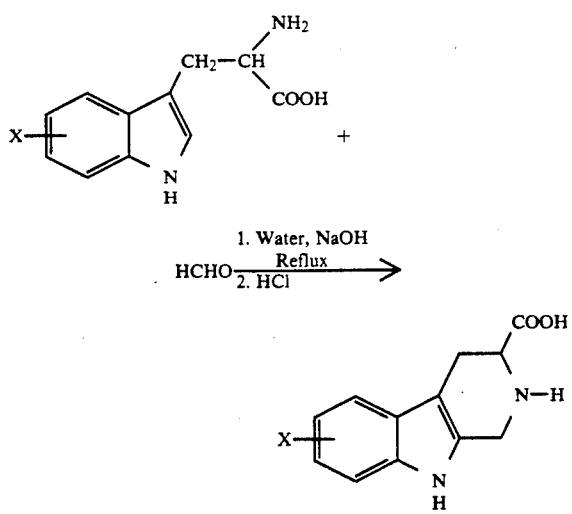

The tryptophan derivative is refluxed with formaldehyde in water in the presence of base and subsequently neutralized to give the desired product (see, Lippke, et al., *J. Med. Chem..* 26, 499–503, 1983). It should be noted that this reaction proceeds with retention of stereochemistry of the tryptophan. Thus, if the starting material is of the D- or L- configuration, the resulting product will be of the (R) or (S) configuration, respectively (see, J. Sandrin, et al., *J. Org. Chem.*, 54, 5636–5640, 1989).

The basic amine nitrogen of the ring may then be protected by standard methods.

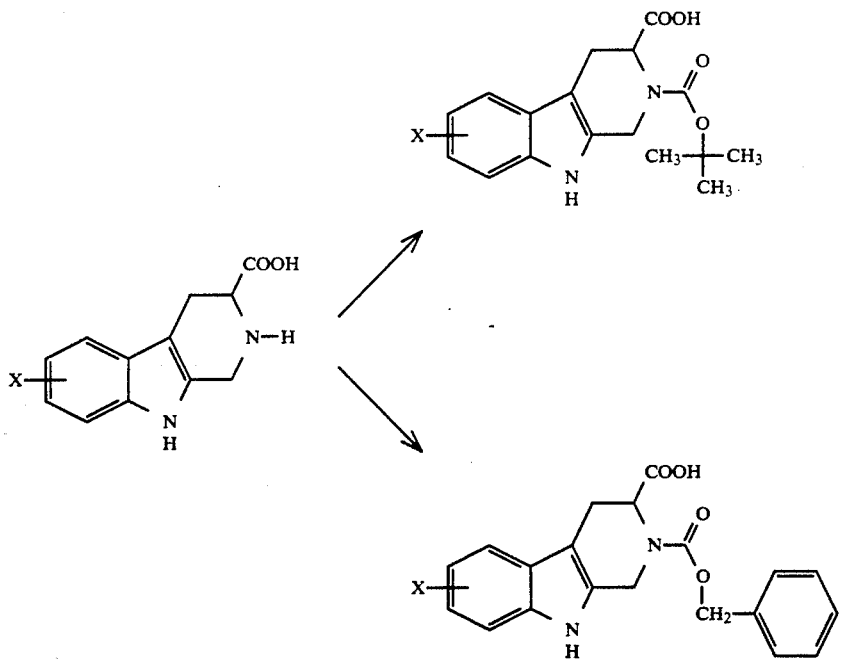

Thus, the BOC group may be introduced by treating the carboline with di-t-butyl dicarbonate in the presence of sodium carbonate or potassium carbonate in solution of tetrahydrofuran and water. Likewise the CBZ group may be introduced using benzyl chloroformate in place of di-t-butyl dicarbonate.

The amine derivative to be used in the coupling reaction may be an aliphatic or aromatic amine or an amino acid, peptide, or amino acid or peptide derivative. The amines, amino acids, peptides or derivatives are available commercially or may be prepared by standard organic chemical or peptide synthetic techniques.

Following the coupling reaction, the blocking group on the ring nitrogen may be removed. In the case of the BOC group, this may be accomplished by treatment with trifluoroacetic acid. The CBZ group may be removed under catalytic hydrogenolysis conditions, such as treatment with hydrogen in ethanol or methanol in the presence of a palladium on carbon catalyst. After deprotection, further derivatization may be accomplished if desired.

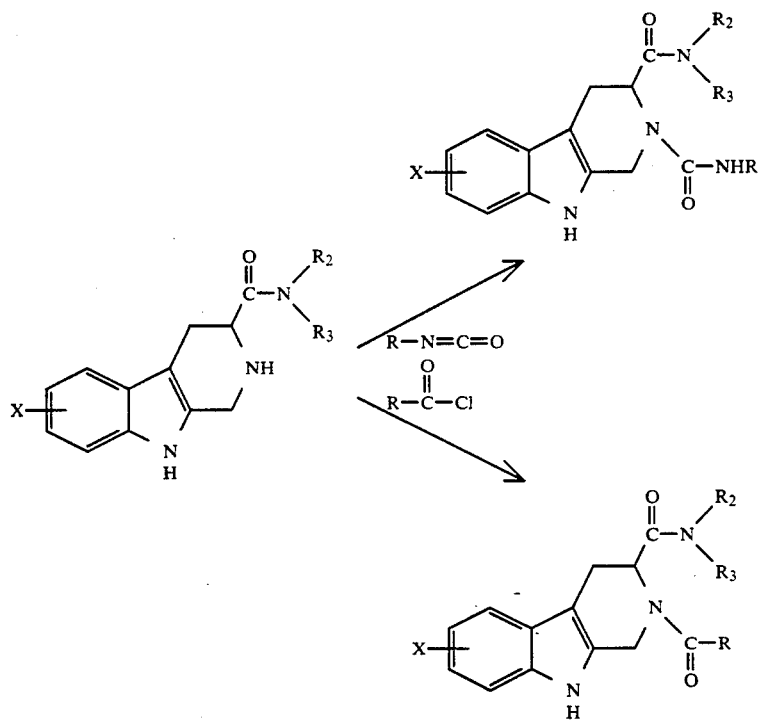

A carbamoyl function may be introduced by treating the deprotected compound with the appropriate alkyl or aryl isocyanate in a solvent such as THF or DMF. An acyl or aroyl function may be introduced by treatment with the appropriate acid halide, in solvents such as THF or methylene chloride, in the presence of a base such as triethylamine.

If protecting groups are necessary to prevent cross reaction with the side chain at the 3-position, these could be retained or removed by standard procedures to give the final product.

All starting materials and intermediates necessary for the preparation of the compounds of the present invention may be obtained commercially or prepared by standard methods.

The invention will now be explained further by the following illustrative example.

EXAMPLE 1

N-[(3R)-1,2,3,4-Tetrahydro-9H-pyrido3,4-b1indole-3-carboxy]-L-leucyl-L-aspartic acid amide.

A. 26.2 g N-tert-butoxycarbonyl-L-aspartic acid β-benzyl ester is dissolved in 500 ml anhydrous tetrahydrofuran and 8.2 g 4-methylmorpholine is added to the solution which is then cooled to $-15°$ C. 8.80 g ethyl chloroformate is added over 5 minutes and the mixture stirred at $-15°$ C. for 45 minutes. 5.45 ml of concentrated ammonium hydroxide solution (28-30%) is added and the mixture is stirred at room temperature for 17 hours. The mixture is then evaporated in vacuo and the residue taken up in 2.2 L of ethyl acetate. The ethyl acetate solution is washed with sodium carbonate solution, water, brine, dried over sodium sulfate, filtered and evaporated in vacuo. The residue is stirred in ether and the resulting solid collected by filtration to give N-tert-butoxycarbonyl-L-aspartic acid amide β-benzyl ester, m.p. 158°-159° C.

B. 220 ml of trifluoroacetic acid is cooled in an ice bath and 22.0 g BOC-L-aspartic acid amide β-benzyl ester is added over a period of 5 minutes. The solution is stirred at room temperature for 1 hour, evaporated in vacuo and the residue triturated in ether to give L-aspartic acid amide β-benzyl ester trifluoroacetate.

C. 10.0 g L-aspartic acid amide β-benzyl ester trifluoroacetate, 6.88g BOC-L-leucine, 5.98 g 1-(3-dimethylaminopropyl)-3-ethylcarbodiimide hydrochloride (EDC), and 4.22 g 1-hydroxybenzotriazole (HBT) are dissolved together in 50 ml dimethylformamide followed by the addition of 6.30 g triethylamine. The mixture is stirred at room temperature for 18 hours, then evaporated in vacuo at 40° C./1 mm Hg. The residue is taken up in 500 ml of ethyl acetate and washed with 10% citric acid solution, 10% sodium carbonate solution, water, brine, and dried over sodium sulfate. The solution is filtered, evaporated and the residue triturated in ether to give a solid, N-tert-butoxycarbonyl-L-leucyl-L-aspartic acid amide β-benzyl ester.

D. 7.37 g BOC-L-leucyl-L-aspartic acid amide β-benzyl ester is stirred into 75 ml trifluoroacetic acid which had been cooled in an ice bath. The ice bath is removed and the solution stirred at room temperature for 45 minutes. The solution is evaporated in vacuo and the oil residue dissolved in 200 ml of ethyl acetate. The solution is washed with sodium carbonate solution, dried over sodium sulfate, filtered, evaporated, and the residue triturated with ether to give L-leucyl-L-aspartic acid amide β-benzyl ester, m.p. 89°–94° C.

E. 20.0 g D-tryptophan is suspended in 40 ml of water and 7.83 g 50%(w/w) sodium hydroxide solution is added and this mixture is stirred to give a clear solution. 7.95 g 37% formaldehyde is added and this mixture is stirred for 2 hours at room temperature, then refluxed for 3 hours. The hot solution is poured into 200 ml water and, with vigorous stirring, the pH is adjust to 5 with 6N hydrochloric acid, giving a precipitate. The slurry is stirred for 18 hours, filtered, and the solid dried at 70° C./0.1 mm Hg overnight to give 18.5 g (3R)-1,2,3,4-tetrahydro-9H-pyrido[3,4-b]indole-3-carboxylic acid.

F. 8.73 g di-t-butyl dicarbonate and 8.65 g (3R)-1,2,3,4-tetrahydro-9H-pyrido[3,4-b]indole-3-carboxylic acid are dissolved together in 150 ml tetrahydrofuran and 5.53 g potassium carbonate is added along with 150 ml of water. The mixture is stirred vigorously overnight. The mixture is evaporated in vacuo to remove most of the THF and the aqueous residue is acidified with 1N hydrochloric acid. This is extracted with ethyl acetate and the organic solution washed with brine, dried over sodium sulfate, filtered, and evaporated. The residue is evaporated from acetonitrile to give (3R)-2-tert-butoxycarbonyl-1,2,3,4-tetrahydro-9H-pyrido[3,4-b]indole-3-carboxylic acid.

G. 0.47 g (3R)-2-BOC-1,2,3,4-tetrahydro-9H-pyrido[3,4-b]indole-3-carboxylic acid, 0.50 g L-leucyl-L-aspartic acid amide β-benzyl ester, 0.211 g HBT, and 0.299 g EDC are dissolved together in 2.5 ml dimethylformamide followed by the addition of 0.158 g triethylamine. The mixture is stirred at room temperature overnight, then evaporated in vacuo. The residue is taken into 50 ml ethyl acetate and the solution washed with 10% citric acid solution, 10% sodium carbonate solution, water, brine, and dried over sodium sulfate. The solution is filtered, evaporated to N-[(3R)-2-tert-butoxycarbonyl-1,2,3,4-tetrahydro-9H-pyrido[3,4-b]indole-3-carboxyl]-L-leucyl-L-aspartic acid amide-β-benzyl ester.

H. 0.85 g N-[(3R)-2-BOC-1,2,3,4-tetrahydro-9H-pyrido[3,4,-b]indole-3-carboxyl]-L-leucyl-L-aspartic acid amide-β-benzyl ester is dissolved in 8.5 ml trifluoroacetic acid and stirred at room temperature for 30 minutes. The solution is evaporated in vacuo and the residue stirred with 10% sodium carbonate solution/ethyl acetate, giving a solid which is collected, washed and dried giving 0.56 g N-[(3R)-1,2,3,4-tetrahydro-9H-pyrido[3,4-b]indole-3-carboxyl]L-leucyl-L-aspartic acid amide β-benzyl ester, m.p. 189°–191° C.

I. 0.51 g of the product from Example 1H is dissolved in 200 ml methanol and 0.10 g 10% palladium on carbon is added. The mixture is stirred under hydrogen at atmospheric pressure for 3 hours. The mixture is filtered, and the filtrate evaporated. The residue is stirred with ethylacetate and the resulting solid collected to give 0.26 g N-[(3R)-1,2,3,4-tetrahydro-9H-pyrido[3,4-b]indole-3-carboxyl]-L-leucyl-L-aspartic acid amide, m.p. 208°–211° C.

EXAMPLE 2

N-[(3S)-1,2,3,4-Tetrahydro-9H-pyrido3,4-b1indole-3-carboxy]-L-leucyl-L-aspartic acid amide A. When L-tryptophan is substituted for D-tryptophan in Example 1E, (3S)-1,2,3,4-tetrahydro-9H-pyrido[3,4-b]indole-3-carboxylic acid is obtained.

B. When (3S)-1,2,3,4-tetrahydro-9H-pyrido[3,4-b]indole-3-carboxylic acid is substituted for the acid in Example 1F, and the resulting product treated as in Examples 1G,H and I, N-[(3S)-1,2,3,4-tetrahydro-9H-pyrido[3,4-b]indole-3-carboxyl]-L-leucyl-L-aspartic acid amide, m.p. 202°–205° C. is obtained.

EXAMPLE 3

N-(3R)-1,2,3,4-Tetrahydro-9H-pyrido3,4-b1indole-3-carboxy]-L-aspartic acid amide A. 5.00 g (3R)-1,2,3,4-Tetrahydro-9H-pyrido[3,4-b]-indole-3-carboxylic acid is suspended in 50 ml water/50 ml tetrahydrofuran and 5.15 g sodium carbonate is added. The mixture is stirred for 5 minutes and 3.94 g benzyl chloroformate is added and the mixture stirred overnight. The mixture is evaporated in vacuo to remove the THF, the aqueous residue acidified with 1N hydrochloric acid and the resulting solid extracted into ethyl acetate. The organic solution is washed with 1N HCl, water, brine, and dried over sodium sulfate. The solution is filtered, evaporated and the residue crystallized from toluene to give (3R)-2-carbobenzoxy-1,2,3,4-tetrahydro-9H-pyrido[3,4-b]indole-3-carboxylic acid, m.p. 181°–184° C.

B. 1.00 g (3R)-2-CBZ-1,2,3,4-tetrahydro-9H-pyrido[3,4-b]indole-3-carboxylic acid, 0.96 g L-aspartic acid amide β-benzyl ester trifluoroacetate, 0.405 g HBT and 0.574 g EDC is dissolved in 4 ml of dimethylformamide, 0.61 g triethylamine is added and the mixture stirred at room temperature overnight. The mixture is worked up as in Example 1C, and the crude product so obtained is purified by flash chromatography on silica gel in ethyl acetate to give N-[(3R)-2-carbobenzoxy-1,2,3,4-tetrahydro-9H-pyrido[3,4-b]indole-3-carboxyl]-L-aspartic acid amide β-benzyl ester.

C. 1.10 g of the product from Example 3B is dissolved in 100 ml methanol and 0.10 g 10% palladium on carbon is added. The mixture is stirred under hydrogen at atmospheric pressure for 5 hours, filtered, evaporated and the residue purified by flash chromatography on silica gel in ethyl acetate/methanol/water, 6:3:1, to give N-[(3R)-1,2,3,4-tetrahydro-9H-pyrido[3,4-b]-indole-3-carboxyl]-L-aspartic acid amide, m.p. 200°–202° C.

EXAMPLE 4

N-(3S)-1,2,3,4-tetrahydro-9H-pyrido3,4-b1indole-3-carboxy]-L-aspartic acid amide When (3S)-1,2,3,4-tetrahydro-9H-pyrido[3,4-b]indole-3-carboxylic acid is substituted for the acid in Example 3A, and the resulting product treated as in Examples 3B and 3C, N-[(3S)-1,2,3,4-tetrahydro-9H-pyrido[3,4-b]indole-3-carboxyl]-L-aspartic amide, m.p. 177°–181° C., is obtained.

EXAMPLE 5

(3R)-3-(2,2′-Diphenyl)ethylcarbamoyl-1,2,3,4-tetrahydro-9H-pyrido3,4-b1indole

A. 1.00 g (3R)-2-CBZ-1,2,3,4-tetrahydro-9H-pyrido[3,4-b]indole-3-carboxylic acid, 0.536 g 2,2- diphenylethylamine, 0.574 g EDC and 0.404 g HBT are dissolved together in 4 ml of dimethylformamide, 0.303 g of triethylamine added, and the mixture stirred at room temperature for 18 hours. The mixture is evaporated and the residue taken up in ethyl acetate and this washed with 10% citric acid solution, 10% sodium carbonate, water, brine, and dried over sodium sulfate. The solution is filtered and evaporated to (3R)-2-carbobenzoxy-3-(2,2-diphenyl)ethylcarbamoyl-1,2,3,4-tetrahydro-9H-pyrido[3,4-b]indole.

B. 1.40 g of the product from Example 5A is dissolved in 40 ml of absolute ethanol, 0.14 g 10% palladium on carbon added, and the mixture stirred under hydrogen at atmospheric pressure for 3 hours. The mixture is filtered, evaporated and the residue stirred with boiling ethyl acetate, cooled and filtered to give (3R)-3-(2,2'-diphenyl)ethylcarbamoyl-1,2,3,4-tetrahydro-9H-pyrido[3,4-b]indole, m.p. 208°–209° C.

EXAMPLE 6

(3R)-3-Diphenylmethylcarbamoyl-1,2,3,4-tetrahydro-9H-pyrido[3,4-b]indole

A. 1.58 g (3R)-2-BOC-1,2,3,4-tetrahydro-9H-pyrido[3,4-b]indole-3-carboxylic acid, 0.915 g aminodiphenylmethane, 1.01 g EDC, and 0.709 g HBT are dissolved together in 6 ml DMF and 0.53 g triethylamine is added. The mixture is stirred at room temperature overnight and worked as in Example 5A to give 2.20 g (3R)-2-tert-butoxycarbonyl-3-diphenylmethylcarbamoyl-1,2,3,4-tetrahydro-9H-pyrido[3,4-b]indole.

B. 2.10 g of the product from Example 6A is dissolved in 21 mol of trifluoroacetic acid and the solution stirred at room temperature for 1 hour. The solution is evaporated and the residue dissolved in ethyl acetate. This solution is washed with sodium carbonate solution, water, brine and dryed over sodium sulfate. The solution is filtered, evaporated and the residue crystallized from ethanol to give (3R)-3-diphenylmethylcarbamoyl-1,2,3,4-tetrahydro-9H-pyrido[3,4-b]indole, m.p. 191°–196° C.

EXAMPLE 7

N-[(3R)-2-benzoyl-1,2,3,4-tetrahydro-9H-pyrido[3,4-b]indole-3-carboxy]-L-aspartic acid amide β-benzyl ester A. 1.00 g (3S)-2-BOC-1,2,3,4-tetrahydro-9H-pyrido[3,4-b]indole-3-carboxylic acid, 1.06 g L-aspartic acid β-benzyl ester trifluoroacetate, 0.636 g EDC, and 0.449 g HBT are combined in 5 ml of DMF, along with 0.68 g triethylamine and treated as in Example 3B to give N-[(3R)-2-tert-butoxycarbonyl-1,2,3,4-tetrahydro-9H-[pyrido[3,4-b]indole-3-carboxyl]-L-aspartic acid amide β-benzyl ester.

B. 1.04 g of the product from Example 7A is dissolved in 10 ml trifluoroacetic acid and stirred at room temperature for 15 minutes. The solution is evaporated and the residue stirred with 25 ml 10% sodium carbonate solution. The resulting solid is collected, washed with water, and dried to give N-[(3R)-1,2,3,4-tetrahydro-9H-pyrido[3,4-b]indole-3-carboxyl]-L-aspartic acid amide β-benzyl ester.

C. 0.50 g of the product from Example 7B and 0.33 g triethylamine are dissolved together in 20 ml tetrahydrofuran, and 0.18 g benzoyl chloride is added. The mixture is stirred at room temperature for 20 minutes. The mixture is evaporated and the residue taken up in 50 ml ethyl acetate and this solution is washed with 1N HCl, water, brine, and dried over sodium sulfate. This solution is filtered, evaporated, and the residue triturated in ether to give N-[(3R)-2-benzoyl-1,2,3,4-tetrahydro-9H-pyrido[3,4-b]indole-3-carboxyl]-L-aspartic acid amide β-benzyl ester, which contained 1.2% (w/w) water, m.p. 110°–120° C. Elemental analysis: Calc'd: C, 67.84; H, 5.51; N, 10.55; Found: C, 67.86; H, 5.53; N, 10.29.

EXAMPLE 8

N-[(3R)-2-benzoyl-1,2,3,4-tetrahydro-9H-pyrido3,4-b]indole-3-carboxyl]-L-aspartic acid amide 0.45 g of N-[(3R)-1,2,3,4-tetrahydro-9H-pyrido[3,4-b]indole-3-carboxyl]-L-aspartic acid amide and 0.41 g triethyl amine are dissolved together in 4 ml of water/tetrahydrofuran (1:1). 0.21 g benzoyl chloride is added and the solution stirred for 30 minutes. The solution is evaporated and the residue stirred with 1N HCl to give a solid. The solid is dissolved in 0.5 N NaOH and the solution is washed with ethyl acetate. The solution is then acidified, extracted with ethyl acetate and the organic solution is washed with water, brine, dried and evaporated. The residue is triturated in ether to give a white solid, N-[(3R)-2-benzoyl-1,2,3,4-tetrahydro-9H-pyrido[3,4-b]indole-3-carboxyl]-L-aspartic acid amide, m.p. 160° C. (dec.).

EXAMPLE 9

N-[(3R)-2-benzoyl-1,2,3,4-tetrahydro-9H-pyrido[3,4-b]indole-3-carboxy]-L-leucyl-L-aspartic acid amide When N-[(3R)-1,2,3,4-tetrahydro-9H-pyrido[3,4-b]indole-3-carboxyl]-L-leucyl-L-aspartic acid amide is substituted for the amide in Example 8, N-[(3R)-2-benzoyl-1,2,3,4-tetrahydro-9H-pyrido[3,4-b]indole-3-carboxyl]-L-leucyl-L-aspartic acid amide, m.p. 155°–160° C., is obtained.

EXAMPLE 10

N-[(3R)-2-(2-naphthoyl)-1,2,3,4-tetrahydro-9H-pyrido[3,4-b]indole-3-carboxy]-L-leucyl-L-aspartic acid amide When 2-naphthoyl chloride is substituted for benzoyl chloride in Example 9, N-[(3R)-2-(2-naphthoyl)-1,2,3,4-tetrahydro-9H-pyrido[3,4-b]indole-3-carboxyl]-L-leucyl-L-aspartic acid amide, m.p. 162°–166° C., is obtained.

EXAMPLE 11

N-[(3R)-2-(3-Methylphenylcarbamoyl)-1,2,3,4-tetrahydro-9H-pyrido[3,4-b]indole-3-carboxy]-L-leucyl L-aspartic acid amide A. 0.30 g N-[(3R)-1,2,3,4-tetrahydro-9H-pyrido[3,4-b]-indole-3-carboxyl]-L-leucyl-L-aspartic acid amide-β-benzyl ester is dissolved in 4 ml of dimethylformamide, 0.075 g m-tolylisocyanate is added and the solution stirred at room temperature for 1 hour. The solution is evaporated at 40° C./2 mmHg, the residue dissolved in ethyl acetate and this solution washed with water, brine, and dried over sodium sulfate. The solution is filtered, evaporated to N-[(3R)-2-(3-methylphenylcarbamoyl)-1,2,3,4-tetrahydro-9H-pyrido[3,4-b]indole-3-carboxyl]-L-leucyl-aspartic acid amide β-benzyl ester, which is used, without further treatment, for the next step.

B. 0.31 g of the product from Example 11A is dissolved in 9 ml absolute ethanol. 0.03 g of 10% palladium on carbon is added and the mixture stirred under hydrogen at room temperature for 3 hours. The mixture is filtered, evaporated, and the residue stirred with 20 ml ether for 3 hours and the resulting solid collected by filtration to give 0.20 g N-[(3R)-2-(3-methylphenylcarbamoyl)-1,2,3,4-tetrahydro-9H-pyrido[3,4-b]indole-3-carboxyl]-L-leucyl-L-aspartic acid amide, m.p. 154°–157° C.

EXAMPLE 12

N-[(3S)-2-(3-methylphenylcarbamoyl)-1,2,3,4-tetrahydro-9H-pyrido]3,4-b]indole-3-carboxy]-L-leucyl-L-aspartic acid amide When N-[(3S)-1,2,3,4-tetrahydro-9H-pyrido[3,4-b]indole-3-carboxyl]-L-leucyl-L-aspartic acid amide β-benzyl ester is substituted for the ester in Example 11A and the resulting product treated as in example 11B, N-[(3S)-2-(3-methylphenylcarbamoyl)-1,2,3,4-tetrahydro-9H-pyrido[3,4-b]indole-3-carboxyl]-L-leucyl-L-aspartic acid amide, m.p. 191°–193° C. is obtained.

EXAMPLE 13

(3R)-3-(N,N-Dipentylcarbamoyl)-2-(3-methylphenylcarbamoyl)-1,2,3,4-tetrahydro-9H-pyrido3,4-b]indole A. 0.40 g (3R)-2-tert-butoxycarbonyl-1,2,3,4-tetrahydro-9H-pyrido[3,4-b]indole-3-carboxylic acid is dissolved in 10 ml tetrahydrofuran. The solution is cooled to −15° C. and 0.127 g triethylamine and 0.386 g N,N-bis[2-oxo-3-oxazolinyl]phosphorodiamidic chloride (BOP-Cl) is added. The mixture is stirred at −15° C. for 20 minutes, then evaporated in vacuo to one-half of the original volume. The mixture is cooled in an ice bath and 0.239 g dipentylamine is added. The mixture is stirred in ice bath temperature overnight. The mixture is evaporated and the residue taken into 50 ml of ethyl acetate and this solution is washed with 1N HCl, 10% sodium bicarbonate solution, water, brine and dried over sodium sulfate. The solution is filtered and evaporated to (3R)-2-tert-butoxy-carbonyl-3-(N,N-dipentyl-carbamoyl)-1,2,3,4-tetrahydro-9H-pyrido[3,4-b]indole.

B. 0.33 g of the product from Example 13A is dissolved in 4 ml trifluoroacetic acid and stirred at room temperature for 30 minutes. The solution is evaporated and the residue dissolved in ethyl acetate and the organic solution washed with sodium carbonate solution, water, brine and dried over sodium sulfate. The solution is filtered, evaporated, and the residue stirred with ether to give a solid, (3R)-3-(N,N-dipentylcarbamoyl)-1,2,3,4-tetrahydro-9H-pyrido[3,4-b]indole, m.p. 157°–158° C.

C. 0.114 g (3R)-3-(N,N-dipentylcarbamoyl)-1,2,3,4-tetrahydro-9H-pyrido[3,4-b]indole is dissolved in 2 ml tetrahydrofuran and 42.7 mg of m-tolylisocyanate is added. The solution is stirred at room temperature for 1 hour, evaporated, and the residue triturated with hexane to give 0.119 g (3R)-3-(N,N-dipentylcarbamoyl)-2-(3-methylphenylcarbamoyl)-1,2,3,4-tetrahydro-9H-pyrido[3,4-b]indole, m.p. 154°–155° C.

EXAMPLE 14

N-[(3R)-2-phenylcarbamoyl-1,2,3,4-tetrahydro-9H-pyrido-[3,4-b]indole-3-carboxy]-L-leucyl-L-aspartic acid amide When phenylisocyanate is substituted for m-tolylisocyanate in Example 11A, and the resulting product treated as in Example 11B, N-[(3R)-2-phenylcarbamoyl-1,2,3,4-tetrahydro-9H-pyrido[3,4-b]indole-3-carboxyl]-L-leucyl-L-aspartic acid amide, m.p. 170° C. (dec.), is obtained.

EXAMPLE 15

Ethyl 4-N-(3R)-2-carbobenzoxy-1,2,3,4-tetrahydro-9H-pyrido[3,4-b]indole-3-carboxyl]aminobenzoate 0.50 g (3R)-2-CBZ-1,2,3,4-tetrahydro-9H-pyrido[3,4-b]indole-3-carboxylic acid is dissolved in 14 ml of tetrahydrofuran/2 ml dimethylformamide, and the mixture cooled to 0° C. 0.14 g N-methyl piperidine, then 0.17 g isopropyl chloroformate are added and the mixture stirred in ice for 5 minutes. 0.22 g ethyl-p-amino benzoate is added and the mixture stirred at room temperature overnight. The mixture is poured into 1N HCl, extracted with ethyl acetate and the organic solution washed with sodium bicarbonate solution, water and brine and dried over magnesium sulfate. The solution is filtered and evaporated and the residue purified by flash chromatography on silica gel in acetone/methylene chloride (1:9) to give ethyl 4-N-[(3R)-2-carbobenzoxy-1,2,3,4-tetrahydro-9H-pyrido[3,4-b]indole-3-carboxyl]aminobenzoate, m.p. 76°–79° C.

EXAMPLE 16

Ethyl 3-N-[(3R)-2-carbobenzoxy-1,2,3,4-tetrahydro-9H-pyrido]3,4-b]indole-3-carboxyl]aminobenzoate When ethyl-3-aminobenzoate is substituted for ethyl-4-aminobenzoate in Example 15, ethyl 3-N-[(3R)-2-carbobenzoxy-1,2,3,4-tetrahydro-9H-pyrido[3,4-b]indole-3-carboxyl]aminobenzoate, m.p. 78°–81° C., is obtained.

EXAMPLE 17

Ethyl 2-N-[(3R)-2-carbobenzoxy-1,2,3,4-tetrahydro-9H-pyrido-]3,4-b]indole-3-carboxyl]aminobenzoate When ethyl-2-aminobenzoate is substituted for ethyl-4-aminobenzoate in Example 15, ethyl 2-N-[(3R)-2-carbobenzoxy-1,2,3,4-tetrahydro-9H-pyrido]3,4-b]indole-3-carboxyl]aminobenzoate, m.p. 79°–82° C., is obtained as the hemihydrate.

EXAMPLE 18

Pyrrolidine-2-N-(3R)-2-carbobenzoxy-1,2,3,4-tetrahydro-9H-pyrido[3,4-b]indole-3-carboxyl]aminobenzamide A. 17.5 g isatoic anhydride and 2.66 g 4-dimethylaminopyridine are combined in 500 ml tetrahydrofuran. 9.32 g of pyrrolidine is added and the mixture is heated at reflux overnight. The mixture is concentrated in vacuo, the residue taken into ethyl acetate and the organic solution washed with citric acid solution, water and brine and dried over magnesium sulfate. The solution is filtered, evaporated and the residue triturated in ether/hexane (1:5) to give N-(2-aminobenzoyl)pyrrolidine, m.p. 79°–81° C.

B. When N-(2-aminobenzoyl)pyrrolidine is substituted for ethyl-4-aminobenzoate in Example 15, pyrrolidine-2-N-[(3R)-2-carbobenzoxy-1,2,3,4-tetrahydro-9H-pyrido-[3,4-b]indole-3-carboxyl]aminobenzamide, m.p. 95°–98° C., is obtained.

EXAMPLE 19

Pyrrolidine-2-N-[(3S)-2-carbobenzoxy-1,2,3,4-tetrahydro-9H-pyrido[3,4-b]indole-3-carboxyl]aminobenzamide When (3S)-2-CBZ-1,2,3,4-tetrahydro-9H-pyrido[3,4-b]-indole-3-carboxylic acid is substituted for the acid in Example 18B, pyrrolidine-2-N-[(3S)-2-carbobenzoxy-1,2,3,4-tetrahydro-9H-pyrido[3,4-b]indole-3-carboxyl]aminobenzamide, m.p. 77°–80° C., is obtained.

EXAMPLE 20

Pyrrolidine-2-N-(3R)-2-(2-naphthoyl)-1,2,3,4-tetrahydro-9H-pyrido[3,4-b]indole-3-carboxyl]aminobenzamide A. 0.80 g of pyrrolidine-2-N-[(3R)-2-carbobenzoxy-1,2,3,4-tetrahydro-9H-[3,4-b]indole-3-carboxyl]aminobenzamide is dissolved in 10 ml of methanol and 9.20 g 10% palladium on carbon is added. The solution is stirred under hydrogen at atmospheric pressure at room temperature overnight. The mixture is filtered and evaporated to pyrrolidine-2-N-[(3R)-1,2,3,4-tetrahydro-9H-pyrido[3,4-b]indole-3-carboxyl]aminobenzamide.

B. 0.150 g of the product from Example 20A is dissolved in 5 ml methylene chloride and the solution cooled to 0° C. 0.012 g triethylamine is added, followed by the addition of 0.08 g 2-naphthoyl chloride. The mixture is stirred at 0° C. for 1 hour, then at room temperature overnight. The mixture is concentrated in vacuo. The residue is taken up in ethyl acetate and the organic solution is washed with citric acid solution, saturated sodium bicarbonate solution and brine and dried over magnesium sulfate. This is filtered and evaporated to a solid, to give pyrrolidine-2-N-[(3R)-2-(2-naphthoyl)-1,2,3,4-tetrahydro-9H-pyrido[3,4-b]indole-3-carboxyl]aminobenzamide., m.p. 113°–115° C.

EXAMPLE 21

Pyrrolidine-2-N-[(3R)-2-(4-methoxyphenylcarbamoyl)-1,2,3,4-tetrahydro-9H-pyrido[3,4-b]indole-3-carboxyl]aminobenzamide 0.150 g of pyrrolidine-2-N-[(3R)-1,2,3,4-tetrahydro-9H-pyrido[3,4-b]indole-3-carboxyl]aminobenzamide is dissolved in 5 ml anhydrous methylene chloride/0.5 ml DMF and 0.06 g p-methoxyphenylisocyanate is added. The mixture is stirred at room temperature overnight, evaporated in vacuo and the residue dissolved in ethyl acetate. The organic solution is washed with 1N HCl, water and brine and dried over magnesium sulfate, filtered and evaporated to obtain a residue. The residue is triturated in ether to give pyrrolidine-2-N-[(3R)-2-(4-methoxyphenylcarbamoyl)-1,2,3,4-tetrahydro-9H-pyrido[3,4-b]indole-3-carboxyl]aminobenzamide, m.p. 159°–162° C.

EXAMPLE 22

Di-N-pentyl-2-N-[(3R)-2-carbobenzoxy-1,2,3,4-tetrahydro-9H-pyrido3,4-b]indole-3-carboxyl]anthranilamide A. 2.0 g isatoic anhydride is dissolved in 50 ml methylene chloride/5 ml dimethylformamide and 1.87 g 4-dimethylaminopyridine and 1.98 g dibutylamine are added. The mixture is stirred at room temperature for 5 hours, then diluted with 250 ml of ethyl acetate. The organic solution is washed with 10% HCl and brine and dried over sodium sulfate followed by filtration and evaporation to obtain a residue. The residue is dissolved in 25 ml ethyl acetate, the solution filtered, concentrated and this residue purified by flash chromatography on silica gel in ethyl acetate/hexane, 2:3, to give 2-amino-N,N-dibutyl benzamide.

B. When 2-amino-N,N-dibutyl benzamide is substituted for ethyl-p-aminobenzoate in Example 15, Di-N-pentyl-2-N-[(3R)-2-carbobenzoxy-1,2,3,4-tetrahydro-9H-pyrido[3,4-b]indole-3-carboxyl]anthranilamide, m.p. 80°–81° C., is obtained.

EXAMPLE 23

Ethyl 2-N[(3S)-2-carbobenzoxy-1,2,3,4-tetrahydro-9H-pyrido[3,4-b]indole-3-carboxyl]aminobenzoate When (3S)-2-CBZ-1,2,3,4-tetrahydro-9H-pyrido[3,4-b]indole-3-carboxylic acid is substituted for the (3R)-carboxylic acid in Example 17 ethyl 2-N-[(3S)-2-carbobenzoxy-1,2,3,4-tetrahydro-9H-pyrido[3,4-b]indole-3-carboxyl]aminobenzoate, m.p. 93°–94° C. is obtained.

EXAMPLE 24

N-(3R)-2-(3,4-dichlorophenylcarbamoyl)-1,2,3,4-tetrahydro-9H-pyrido[3,4-b]indol-3-yl]carbonyl-L-isoleucyl-L-aspartic acid amide A. When Boc-L-isoleucine is substituted for Boc-L-leucine in Example 1C, (3R)-1,2,3,4-tetrahydro-9H-pyrido[3,4-b]indole-3-carboxylic acid is obtained.

B. When 3,4-dichlorophenyl isocyanate is substituted for m-tolyl isocyanate in Example 11A and the resulting product is treated as in Example 11B, N-[(3R)-2-(3,4-dichlorophenylcarbamoyl)-1,2,3,4-tetrahydro-9H-pyrido[3,4-b]indol-3-yl]carbonyl-L-isoleucyl-L-aspartic acid amide, m.p. 155°–158° C., is obtained.

EXAMPLE 25

N-(3R)-2-(3,4-dichlorophenylcarbamoyl)-1,2,3,4-tetrahydro-9H-pyrido[3,4-b1indol-3-yl]carbonyl-L-prolyl-L-aspartic acid amide When Boc-L-proline is substituted for Boc-L-isoleucine in Example 24A, N-(3R)-2-(3,4-dichlorophenylcarbamoyl)-1,2,3,4-tetrahydro-9H-pyrido[3,4-b]indol-3-yl]carbonyl-L-prolyl-L-aspartic acid amide, m.p. 141° C., is obtained.

EXAMPLE 26

N-(3R)-2-(3,4-dichlorophenylcarbamoyl)-1,2,3,4-tetrahydro-9H-pyrido3,4-b1indol-3-yl]carbonyl-1'amino-1'cyclopentylcarbonyl-L-aspartic acid amide When Boc-1-amino-1-cyclopentane carboxylic acid is substituted for Boc-L-proline in Example 25, N-(3R)-2-(3,4-dichlorophenylcarbamoyl)-1,2,3,4-tetrahydro-9H-pyrido[3,4-b]indol-3-yl]carbonyl-1'amino-1'cyclopentyl-carbonyl-L-aspartic acid amide, m.p. 168° C., is obtained.

EXAMPLE 27

N-(3R)-2-(3,4-dichlorophenylcarbamoyl)-1,2,3,4-tetrahydro-9H-pyrido[3,4-b1indol-3-yl]carbonyl-L-leucyl-β-alanine A. When β-alanine benzyl ester trifluoroacetate is substituted for L-aspartic acid amide trifluoroacetate in Example 1C, Boc-L-leucine-β-alanine benzyl ester is obtained.

B. When 3,4-dichlorophenyl isocyanate is substituted for m-tolyl isocyanate in Example 11A and the resulting product is treated as in Example 11B, N-(3R)-2-(3,4-dichlorophenylcarbamoyl)-1,2,3,4-tetrahydro-9H-pyrido[3,4-b]indol-3-yl]carbonyl-L-leucyl-β-alanine, m.p. 115°–117° C., is obtained.

EXAMPLE 28

N-(3R)-2-(3,4-dichlorophenylcarbamoyl)-1,2,3,4-tetrahydro-9H-pyrido[3,4-b]indol-3-yl]carbonyl-L-leucyl-glucinamide A. When glycinamide hydrochloride is substituted for L-aspartic acid amide trifluoroacetate in Example 1C, Boc-L-leucine-glycinamide is obtained.

B. When 3,4-dichlorophenylisocyanate is substituted for m-tolyl isocyanate in Example 11A, N-(3R)-2-(3,4-dichlorophenylcarbamoyl)-1,2,3,4-tetrahydro-9H-pyrido[3,4-b]indol-3-yl]carbonyl-L-leucyl-glucinamide, m.p. 142°–145° C., is obtained.

Using appropriate starting materials and analogous procedures used in the previous examples, the following compounds are made:

EXAMPLE 29

N-[(3R)-2-(3-methylcarbamoyl)-1,2,3,4-tetrahydro-9H-pyrido[3,4-b-9 indol-3-yl]carbonyl-L-leucyl-L-O-benzylserine

EXAMPLE 30

N-[(3R)-2-(2,3-dichlorophenylcarbamoyl)-1,2,3,4-tetrahydro-9H-pyrido[3,4-b]indol-3-yl]carbonyl-L-leucyl-glycinamide

EXAMPLE 31

N-[(3R)-2-(3,4-dichlorophenylcarbamoyl)-1,2,3,4-tetrahydro-9H-pyrido[3,4-b]indol-3-yl]carbonyl-L-leucinecyclohexylamide

EXAMPLE 32

N-[(3R)-2-(2,3-dichlorophenylcarbamoyl)-1,2,3,4-tetrahydro-9H-pyrido[3,4-b]indol-3-yl]carbonyl-L-leucyl-β-alanine

EXAMPLE 33

N-[(3R)-2-(3-methylphenylcarbamoyl)-1,2,3,4-tetrahydro-9H-pyrido[3,4-b]indol-3-yl]carbonyl-L-leucyl-glycinamide

EXAMPLE 34

N-[(3R)-2-(3-methylphenylcarbamoyl)-1,2,3,4-tetrahydro-9H-pyrido[3,4-b]indol-3-yl]carbonyl-L-leucyl-β-alanine

EXAMPLE 35

N-(3R)-2-(2,3-dichlorphenylcarbamoyl)-1,2,3,4-tetrahydro-9H-pyrido3,4-b]indol-3-yl]carbonyl-L-leucyl-L-aspartic acid amide

EXAMPLE 36

N-(3R)-2-(4-methoxyphenylcarbamoyl)-1,2,3,4-tetrahydro-9H-pyrido[3,4-b]indol-3-yl]carbonyl-L-leucyl-L-aspartic acid amide

EXAMPLE 37

N-(3R)-2-(3-methylcarbamoyl)-1,2,3,4-tetrahydro-9H-pyrido[3,4-b]indol-3-yl]carbonyl-L-isoleucyl-L-aspartic acid amide

EXAMPLE 38

N-[(3R)-2-(3-methylphenylcarbamoyl)-1,2,3,4-tetrahydro-9H-pyrido[3,4-b]indol-3-yl]carbonyl-L-leucyl-D-aspartic acid amide

EXAMPLE 39

N-[(3R)-2-(3-methylphenylcarbamoyl)-1,2,3,4-tetrahydro-9H-pyrido[3,4-b]indole-3-carboxy]-L-leucinamide

EXAMPLE 40

N-[(3R)-1,2,3,4-tetrahydro-9H-pyrido3,4-b]indole-3-carboxyl]-L-leucyl-L-aspartic acid amide-β-benzyl ester

EXAMPLE 41

N-[(3R)-2-benzoyl-1,2,3,4-tetrahydro-9H-pyrido[3,4-b]indole-3-carboxy]-L-aspartic acid amide-β-benzyl ester

EXAMPLE 42

N-[(3R)-2-(3-methylphenylcarbamoyl)-1,2,3,4-tetrahydro-9H-pyrido[3,4-b]indole-3-carboxy11-L-leucyl-L-phenylalanine amide

EXAMPLE 43

Ethyl 4-N-[(3R)-2-(3-methylphenylcarbamoyl)-1,2,3,4-tetrahydro-9H-pyrido3,4-b]indole]aminobenzoate

EXAMPLE 44

N-[(3R)-2-(3-methylphenylcarbamoyl)-1,2,3,4-tetrahydro-9H-pyrido[3,4-b]indole-3-carboxyl]-L-prolyl-L-aspartic acid amide

EXAMPLE 45

N-(3R)-2-(3-methylphenylcarbamoyl)-1,2,3,4-tetrahydro-9H-pyrido[3,4-b]indole-3-carboxyl]-D-leucyl-D-aspartic acid amide

EXAMPLE 46

N-[(3R)-2-(3-methylphenylcarbamoyl)-1,2,3,4-tetrahydro-9H-pyrido[3,4-b]indole-3-carboxyl]-L-aspartic acid dipentyl amide

EXAMPLE 47

N-(3R)-2-(1-naphthoyl)-1,2,3,4-tetrahydro-9H-pyrido[3,4-b]indole-3-carboxyl]-L-leucyl-L-aspartic acid amide-β-benzyl ester.

EXAMPLE 48

N-(3R)-2-(2-naphthoyl)-1,2,3,4-tetrahydro-9H-pyrido[3,4-b]indole-3-carboxyl]-L-leucyl-L-aspartic acid amide-β-benzyl ester

EXAMPLE 49

N-(3S)-2-(3-methylphenylcarbamoyl)-1,2,3,4-tetrahydro-9H-pyrido[3,4-b]indole-3-carboxyl]-D-leucyl-D-aspartic acid amide

EXAMPLE 50

N-(3R)-2-(3-methylphenylcarbamoyl)-1,2,3,4-tetrahydro-9H-pyrido[3,4-b]indole-3-carboxyl]-L-leucyl-L-asparagine

EXAMPLE 51

N-[(3R)-2-(3-methylphenylcarbamoyl)-1,2,3,4-tetrahydro-9H-pyrido[3,4-b]indole-3-carboxyl]-L-leucyl-D-aspartic acid amide

EXAMPLE 52

N-(3S)-2-(3-methylphenylcarbamoyl)-1,2,3,4-tetrahydro-9H-pyrido[3,4-b]indole-3-carboxyl]-D-leucyl-L-aspartic acid amide

EXAMPLE 53

N-[(3R)-2-(3-methylphenylcarbamoyl)-1,2,3,4-tetrahydro-9H-pyrido[3,4-b]indole-3-carboxyl]N'-methyl-L-leucine-L-aspartic acid amide

EXAMPLE 54

N-[3R)-2-(3-methylbenzoyl)-1,2,3,4-tetrahydro-9H-pyrido[3,4-b]indole-3-carboxyl]-L-leucyl-L-aspartic acid amide

EXAMPLE 55

N-[(3R)-2-(4-chlorophenylcarbamoyl)-1,2,3,4-tetrahydro-9H-pyrido[3,4-b]indole-3-carboxyl]-L-leucyl-L-asartic acid amide

EXAMPLE 56

N-[(3R)-2-(3-methylphenylcarbamoyl)-1,2,3,4-tetrahydro-9H-pyido[3,4-b]indole-3-carboxyl]glycyl-L-aspartic acid amide

EXAMPLE 57

N-[(3R)-2-(3-methylphenylcarbamoyl)-1,2,3,4-tetrahydro-9H-pyrido[3,4-b]indole-3-carboxyl]-D-leucyl-L-aspartic acid amide

EXAMPLE 58

N-(3R)-2-(3-methylcarbamoyl)-1,2,3,4-tetrahydro-9H-pyrido[3,4-b]indole-3-carboxyl]-L-alanyl-L-aspartic acid amide

EXAMPLE 59

N-[(3R)-2-(3,5-dichlorophenylcarbamoyl)-1,2,3,4-tetrahydro-9H-pyrido[3,4-b]indole-3-carboxyl]-L-leucyl-L-aspartic acid amide

EXAMPLE 60

N-[(3R)-2-(3,5-dimethylphenylcarbamoyl)-1,2,3,4-tetrahydro-9H-pyrido[3,4-b]indole-3-carboxyl]-L-leucyl-L-aspartic acid amide N-[(3R)-2-(3-methoxyphenylcarbamoyl)-1,2,3,4-tetrahydro-9H-pyrido3,4-b]indole-3-carboxyl]-L-leucyl-

EXAMPLE 61

L-aspartic acid amide

EXAMPLE 62

N-(3R)-2-(2-naphthylcarbamoyl)-1,2,3,4-tetrahydro-9H-pyrido[3,4-b]indole-3-carboxyl]-L-leucyl-L-aspartic acid amide

EXAMPLE 63

N-(3R)-2-(3-trifluoromethylphenylcarbamoyl)-1,2,3,4-tetrahydro-9H-pyrido[3,4-b]indole-3-carboxyl]-L-leucyl-L-aspartic acid amide

EXAMPLE 64

N-(3R)-2-(3-methylphenylcarbamoyl)-1,2,3,4-tetrahydro-9H-pyrido[3,4-b]indole-3-carboxyl]-O-benzyl-L-seryl-L-aspartic acid amide

EXAMPLE 65

N-(3R)-2-(3-fluorophenylcarbamoyl)-1,2,3,4-tetrahydro-9H-pyrido[3,4-b]indole-3-carboxyl]-L-leucyl-L-aspartic acid amide

EXAMPLE 66

N-(3R)-2-(3,4-dichlorophenylcarbamoyl)-1,2,3,4-tetrahydro-9H-pyrido[3,4-b]indole-3-carboxyl]-L-leucyl-L-aspartic acid amide

EXAMPLE 67

N-[(3R)-2-(1-naphthylcarbamoyl)-1,2,3,4-tetrahydro-9H-pyrido[3,4-b]indole-3-carboxyl]-L-leucyl-L-aspartic acid amide

EXAMPLE 68

N-[(3S)-2-(3-methylphenylcarbamoyl)-1,2,3,4-tetrahydro-9H-pyrido[3,4-b]indole-3-carboxyl]-D-prolyl-D-aspartic acid amide

EXAMPLE 69

N-[(3R)-2-(3,4-dichlorobenzoyl)-1,2,3,4-tetrahydro-9H-pyrido[3,4-b]indole-3-carboxyl]-L-leucyl-L-aspartic acid amide

EXAMPLE 70

N-[(3S)-2-(3,4-dichlorophenylcarbamoyl)-1,2,3,4-tetrahydro-9H-pyrido3,4-b]indole-3-carboxyl]-D-prolyl-D-aspartic acid amide

EXAMPLE 71

N-[(3S)-2-(3,4-dichlorophenylcarbamoyl)-1,2,3,4-tetrahydro-9H-pyrido3,4-b]indole-3-carboxyl]-D-leucyl-D-aspartic acid amide

EXAMPLE 72

N-(3S)-2-(3-methylphenylcarbamoyl)-1,2,3,4-tetrahydro-9H-pyrido[3,4-b]indole-3-carboxyl]-D-leucyl-D-glutamic acid amide

EXAMPLE 73

N-[(3R)-2-(3-methylphenylcarbamoyl)-1,2,3,4-tetrahydro-9H-pyrido[3,4-b]indole-3-carboxyl]-L-leucyl-L-glutamic acid amide

EXAMPLE 74

N-[(3R)-2-(3,4-dichlorophenylcarbamoyl)-1,2,3,4-tetrahydro-9H-pyrido[3,4-b]indole-3-carboxyl]-L-leucyl-L-glutamic acid amide

EXAMPLE 75

N-[2-(3-methylphenylcarbamoyl)-1,2,3,4-tetrahydro-9H-pyrido[3,4-b]indole-3-carboxyl]-L-leucyl-L-aspartic acid amide Biological activity of compounds according to the present invention have been evaluated as described hereunder.

CCK-A RECEPTOR BINDING ASSAY

Materials and Methods

Washer Buffer (for use with Brandel Cell Harvester):
30 liters of 50 mM Tris, ph 7.7: Dissolve 181.7 g. Tris base in 4 l. deionized water at room temperature. Adjust pH to 7.7 with 6 N HCl and Q.S. to 30 l.

Assay Buffer:
50 mM Tris-Cl, 5 mM $MgCl_2$, 5 mM dithio-thretiol, 0.14 mg/ml bacitracin, and 2 mg/ml bovine serum albumin.

1 liter of 5X stock buffer:
30.28 g. Tris base per 800 ml D.I. water 5.09 g. $MgCl_2 6\ H_2O$, pH to 7.7 at room temperature with 6N HCl and Q.S. 1 liter, store at 4° C.

250 ml working buffer kept on ice:
50 ml of 5X stock buffer 0.1928 g. dithiothretiol (5 mM), 35 mg bacitracin (0.14 mg/ml), and 0.5 g. BSA (2mg/ml).

Unlabeled L-364,718(nonpeptide ligand):
Unlabeled L-364,718 (300 nM final concentration) is used to define nonspecific binding. A 3 mM solution is made in absolute ethanol and stored in a scintillation vial at −70° C. Aliquots are diluted 100-fold in the assay.

Receptors Preparation:
A Sprague-Dawley rat is sacrificed by asphyxiation with carbon dioxide and the pancreas removed. The tissue is immersed in cold wash buffer and carefully trimmed of fat, connective tissue, blood vessels, blotted and weighed. The tissue is homogenized in a Sorvall SS-34 centrifuge tube in 50 volumes of wash buffer using a Polytron at setting 7 for 15 seconds. The tissue is centrifuged (Sorvall SS-34) at 19,000 rpm for 10 min. The supernatant is poured off and the pellet resuspended in sufficient buffer to obtain a contraction of 40 mg tissue wet weight/ml. Separate aliquots (2,3ml) are placed in each of 8 centrifuge tubes and centrifuged as before. The supernatants are poured off and the pellets stored at −70° C. Stored pellets are sufficient for the assay of 160 tubes and are stable for 1-2 months.

During the assay the stored membranes are resuspended in 40 ml of assay buffer by scraping the pellet off the wall of the centrifuge tube and washing it into a teflon-glass homogenizer. Membranes are resuspended by 5 passes with the teflon pestle and the membranes stored on ice until ready for use.

Preparation of Compounds:
Compounds are prepared in DMSO (dimethyl sulfoxide) or in assay buffer. The majority of structures active as CCK antagonists generally require DMSO for complete solubility. Approximately 2–3 mg of compound is weighed directly into a 13×100 mm test tube and sufficient DMSO added to obtain a working stock solution at a concentration 100 fold greater than the highest concentration being tested in the assay. A total of 10 μl of each concentration of drug is added into a final volume of 1 ml to yield a 100 fold dilution of the, working stock solution. Control binding tubes ("totals and nonspecifics") are also treated with 10 μl DMSO.

Radioligand Preparation:
$^3$H-L-364,718 is obtained from New England Nuclear (Cat. #971) and is used as supplied. The final assay concentration of $^3$H-L-364,718 in assay buffer should be 0.2 nM in a final assay volume of 1 ml. $^3$H-L-364,718 (0.2 pmol) is added into the assay in a volume of 25 μl (8 nM working stock solution). The required dilution (usually > 1000 fold) is obtained by dividing the working stock concentration into the concentration of the specific lot.

Assay Procedure:

Samples are prepared in triplicate and a "total" (buffer addition) and "nonspecific" (300 nM unlabeled L-364,718) set of tubes included in each set of 24 tubes. The remaining 6 sets of triplicates are used either for screening or $IC_{50}$ determinations. The order of addition is drugs-DMSO, buffer, unlabeled L-364,718, $^3$H-L-364,718, and to start the assay, membranes.

While tubes are incubating a shaking water bath at 37° C. for 30 min Brandel deposit/dispense filters are presoaked in wash buffer. Following the end of the incubation, sets of 24 tubes are rapidly washed with assay buffer as follows. Assay buffer is added to the incubation tubes to the height of the uppermost cross support in the standard Brandel test tube rack and the contents immediately aspirated. This process is repeated twice more, the filter removed, marked and the next set of 24 tubes processed. It is critical that the filtration-washing step be completed as quickly as possible; preferably within 20 seconds. The individual filter rings from a single filter strip are dispensed into 7 ml minivials and 5 ml of scintillation cocktail (AquaSol 2, Dupont) added using the Brandel deposit/dispenser apparatus. Samples are counted following either 30 min of low speed shaking on a horizontal shaker (Eberbach Corp.) or a prolonged equilibration period (>2 hr) in the scintillation counter (Beckman model 6000IC).

For screening studies, or in the determination of $IC_{50}$ values, results are expressed as the degree of inhibition of specific binding by the addition of an unknown compound. Specific binding is defined as the difference between the counts from "total" and "nonspecific" tubes. The nonspecific binding value is also subtracted from each sample and the specific binding expressed as a percentage of that seen in the absence of drug. For screening (usually at 100 $\mu$M) the percent of specific binding is the desired quantity, whereas for determination of the $IC_{50}$ concentration, one test multiple concentration of drug to define the concentration at which specific binding is reduced 50%.

GASTRIN RECEPTOR BINDING ASSAY

Materials and Methods

Solutions:

(a) Phosphate Buffered Saline (PBS): 8.743 g NaCl, 523 mg $K_2HPO_4$ and 76.8 mg $NaH_2PO_4$ is dissolved in 1.0 liter of deionized water and the pH of the solution is adjusted to 7.3 with 5N NaOH.

(b) Buffer A: While adding Basal Medium Eagle (BME) containing Earle's Salts, L-glutamine and 25 mM HEPES, 3 liters of deionized water is stirred, followed by the addition and dissolution of 6.6 mg of sodium bicarbonate. The solution is then equilibrated with 95% $O_2$/5% $CO_2$ gas followed by titration to a pH of 7.4 with NaOH.

(c) Buffer B: 18.75 mg of collagenase and 25 ml of BSA is dissolved in 25 ml of Buffer A.

(d) Buffer C: 0.3 g of BSA is dissolved in 300 ml of Buffer A.

(e) 6.25 mg Bacitracin is dissolved in 25 ml of Buffer A.

Ligands:

(f) $^{125}$I-(Leu-15)-Gastrin: 100 microcurie dissolved in 2.0 ml of Buffer A to make 50 microcurie/ml.

(g) $^{125}$I-(15-methionine)-Human Gastrin: 50 microcurie/ml.

(h) (Leu 15)-Gastrin: 5.2 mg of (Leu-15)- Gastrin is dissolved in 10 ml of Buffer A. At the time of assay 1:10 dilution is made and 10 $\mu$l assay tube is used.

Preparation of Glands:

A guinea pig (Hartley Strain) weighing 150–200 grams, is sacrificed by $CO_2$ asphyxiation and the stomach immediately excised, cut along the greater curvature, cleaned out and immediately immersed in a beaker containing cold PBS, pH 7.3, to insure thorough cleaning. The fundic mucosa is gently scraped off the submucosa and added to a preweighed 50 ml plastic centrifuge tube containing 30 ml of cold Buffer A. The weight of the plastic centrifuge tube containing the buffer is then subtracted from the combined weight of the mucosa and the buffer-containing tube to give the weight of the mucosa. The weight of the mucosa thus determined is recorded for later calculations.

The mucosa is then washed twice in Buffer A. After the final wash, the tissue is minced and is placed in a 100-ml glass beaker containing about 1.0 ml of Buffer A, and washed twice again by repeated centrifugation at 50×g for 5 minutes each and aspiration of supernatant. The washed tissue fragments are then added to a glass Erlenmeyer flask containing 25 ml of Buffer B and incubated in a Dubnoff shaking water bath at 37° C. for 30 minutes in a 95% $O_2$ - 5% $CO_2$ atmosphere. After the incubation, the digested tissue fragments in the Collegenase-buffer solution are triturated, filtered through a 200-micron nylon mesh and centrifuged at 50×g for 5 minutes. The supernatant is aspirated and discarded, the tissue washed 2× in Buffer C, resuspended in same buffer, incubated in a 37° C. water bath in an atmosphere of 95% $O_2$ - 5% $CO_2$ for 5 minutes, and centrifuged. The pelleted glands are suspended in Buffer D at a desired concentration of 2x10$^5$ glands/ml to use in the receptor binding assay.

The Assay Method:

Six minisorp tubes (16×100 mm) are serially marked and divided into two groups thus: tubes #1, #2, and #3 are marked "T" for "Totals" and tubes #4, #5, and #6 are marked "NS" for "Non-Specifics." Into each of the six tubes are added 220 $\mu$l of prepared glands in Buffer D; 20 $\mu$l of Buffer A in tubes #1, #2, and #3; 10 $\mu$l, in tubes #4, #5 and #6; (10$\mu$ of (Leu-15)-Gastrin (25 $\mu$M) in tubes #4, #5, and #6. The six tubes are then transferred immediately to a 25° C. water bath and challenged each with 10 $\mu$l $^{125}$I-(Leu-15)-Gastrin diluted as per calculation. The tubes are then covered with a gas hood connected to a 95% $O_2$ - 5% $CO_2$ gas source and mechanically agitated in a shaker for 30 minutes.

At the end of the incubation period, the assay mixtures are each filtered through a Whatman glass fiber filter B on a Brandel tissue harvester and washed twice with Buffer A. The filters are pre-soaked in Buffer C before use. The filter strips are removed after the final wash and individual filters counted in a Gamma Counter. The counts from the "Non-Specific" tubes are then averaged and subtracted from the average "Totals" to give the Specific Counts. For screening compounds, the above assay method is utilized except that triplicate tubes are prepared for each concentration of compound to be assayed. 20 $\mu$l of a solution of each compound to be assayed in triplicate are added to each designated tube. In displacement studies the $IC_{50}$ value is the concentration of compound using a 50% decrease in specific binding of a tracer amount of $^{125}$I-(Leu-15)

Gastrin. The $IC_{50}$ value is derived from a plot of the log of the displacer concentration against the percentage of specific binding. Results of testing are shown hereunder in Table I.

TABLE I

In vitro Binding Data
$IC_{50}$ (μM)

| Compounds of Example | CCK | Gastrin |
|---|---|---|
| 1 | >300 | 12 |
| 2 | >300 | 60 |
| 3 | >300 | >300 |
| 4 | >300 | >300 |
| 5 | 50–60 | 59 |
| 6 | 62 | 60 |
| 7 | 25 | — |
| 8 | 82 | 78 |
| 9 | 230 | 25 |
| 10 | 25 | 15 |
| 11 | 34 | 4.0 |
| 12 | 170 | 29 |
| 13 | 10 | >300 |
| 14 | >100 | 5.5 |
| 15 | 9 | 10 |
| 16 | 10–25 | >300 |
| 17 | >10 | 100 |
| 18 | 25 | 55 |
| 19 | 20 | 8 |
| 20 | >30 | 80 |
| 21 | — | 90 |
| 22 | >10 | >300 |
| 23 | >10 | >300 |
| 24 | 36 | .77 |
| 25 | — | .23 |
| 26 | 100 | 1.3 |
| 27 | 14 | .41 |
| 28 | 9 | .91 |
| 39 | >100 | .23 |
| 40 | 41 | 6 |
| 41 | 25 | — |
| 42 | 4.0 | 10.0 |
| 43 | 37 | 30 |
| 44 | 98 | .2.2 |
| 45 | 78 | >10 |
| 46 | 3.9 | 2.6 |
| 49 | 35 | 0.9 |
| 50 | 92 | 12 |
| 51 | 100 | 17 |
| 52 | 53 | >30 |
| 53 | 29.0 | 6.0 |
| 54 | >100 | 6.8 |
| 55 | 48.0 | 3.3 |
| 56 | 34 | >30 |
| 57 | 100 | 22 |
| 58 | 65 | 18 |
| 59 | 34.0 | 2.0 |
| 60 | 65 | 15 |
| 61 | >100 | 6.4 |
| 62 | 9.3 | 1.2 |
| 63 | 86 | 4.1 |
| 64 | 29.0 | 5.3 |
| 65 | >100 | 7.3 |
| 66 | 24 | 0.54 |
| 67 | 100 | 2.0 |
| 71 | — | 4.0 |

Compounds of the present invention are potent antagonists of CCK and gastrin and as such are valuable pharmaceutical agents for mammals for the treatment and prevention of disorders involving CCK or gastrin.

The compounds of the present invention may be administered to a patient in need of such treatment or prevention either alone or in combination with a pharmaceutically acceptable carrier. The compounds may be administered orally or parenterally including intramuscularly, intravenously, intraperitoneally, subcutaneously and topically.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, trouches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compound in such therapeutically useful compositions is such that a suitable dosage will be obtained. Preferred compositions or preparations according to the present invention are prepared so that an oral dosage unit form contains between about 10 and 300 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions the preferred methods of preparation are vacuum drying and the freeze-drying technique which yield a powder of the active ingredient plus any additional desired ingredient from previously sterile-filtered solution thereof.

The physician will determine the dosage of the present therapeutic agents which will be most suitable and it will vary with the forms of administration and the particular compound chosen, and furthermore, it will vary with the particular patient under treatment. He will generally wish to initiate treatment with small dosages substantially less then the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as comparable therapeutic agents and the dosage level is of the same order of magnitude as is generally employed with these other therapeutic agents. The therapeutic dosage will generally be from 0.5 to 750 milligrams per day and higher, and preferably in the range of 0.1 mg/kg to about 75 mg/kg of body weight. Tablets containing from 10 to 250 mg of active agent are particularly useful.

What is claimed is:

1. A compound of the formula

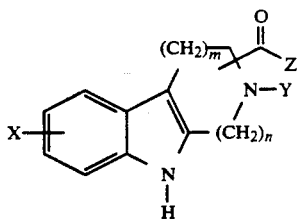

wherein:

X is hydrogen, hydroxy, lower alkyl, hydroxy lower alkyl, lower alkoxy, carboxy, halo, trihalomethyl, amino, lower alkylamino, di lower alkylamino, lower alkanoylamino, cyano, lower alkylcarboxy, formyl, nitro, lower alkanoyloxy, carbamoyl, carb lower alkoxy-lower alkoxy, lower alkynyl, lower alkenyl, lower alkylsulfinyl, lower alkylsulfonyl, lower alkoxycarbonyl, lower alkanoyl, lower alkenoyl, phenyl, naphthyl, or phenyl or naphthyl optionally substituted by a substituent selected from the group consisting of lower alkyl, lower alkoxy, amino, halo, phenyl, naphthyl, phenyloxy, naphthyloxy, carbo lower alkoxy, nitro, di lower alkylamino, trifluoromethyl, thio lower alkyl and carbamoyl;

Y is hydrogen, lower alkyl, carbobenzoxy, tert-butoxycarbonyl,

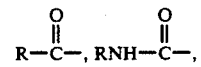

phenyl lower alkyl, or naphthyl lower alkyl;

Z is

where 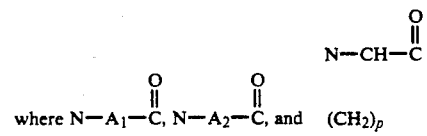

are derived from natural or synthetic amino acids.

B is hydroxy, lower alkoxy, —NR$_4$R$_5$ where R$_4$ and R$_5$ are independently hydrogen or lower alkyl, or B is phenyl lower alkoxy, naphthyl lower alkoxy, phenyloxy, naphthyloxy, or phenyl lower alkoxy, naphthyl lower alkoxy, phenyloxy or naphthyloxy optionally substituted by one or two substituents selected from the group consisting of lower alkyl, lower alkoxy, amino, halo, phenyl, naphthyl, phenyloxy, naphthyloxy, carbo lower alkoxy, nitro, di lower alkylamino, trifluoromethyl, thio lower alkyl and carbamoyl;

m==1;

p is 3, 4, or 5;

R is phenyl, naphthyl, or phenyl or naphthyl optionally substituted by one or two substituents selected from the group consisting of lower alkyl, lower alkoxy, amino, halo, phenyl, naphthyl, phenyloxy, naphthyloxy, carbo lower alkoxy, nitro, di lower alkylamino, trifluoromethyl, thio lower alkyl and carbamoyl; and R$_1$ and R$_2$ are independently hydrogen or lower alkyl;

or a pharmaceutically acceptable salt thereof.

2. A compound of the formula according to claim 1 wherein: X is hydrogen, hydroxy, lower alkyl, hydroxy loweralkyl, F, trifluoromethyl, amino, carboxy or lower alkyl amino;

Y is hydrogen, lower alkyl, carbobenzoxy, tert-butoxycarbonyl, or

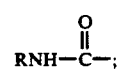

R$_1$ is hydrogen or lower alkyl;

R$_2$ is hydrogen or lower alkyl;

B is hydroxy, lower alkoxy, phenyl lower alkoxy, naphthyl lower alkoxy, or —NR$_4$R$_5$; or a pharmaceutically acceptable salt thereof.

3. A compound according to claim 1 wherein R is phenyl or naphthyl optionally substituted by one or two substituents selected from the group consisting of lower alkyl, lower alkoxy, amino, halo, lower alkanoyl and lower alkanoyloxy.

4. A compound according to claim 1 wherein

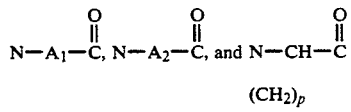

are derived from natural amino acids selected from the group consisting of Gly, Ala, Val, Leu, Ile, Phe, Pro, Ser, Thr, Tyr, Asn, Gln, Lys, Arg, Trp, His, Cys, Met, Asp and Glu.

5. A compound according to claim 1 wherein Y is

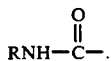

6. A compound according to claim 1 wherein R is phenyl or substituted phenyl.

7. A compound according to claim 6 wherein B is —NR$_4$R$_5$.

8. A compound according to claim 7 of the formula

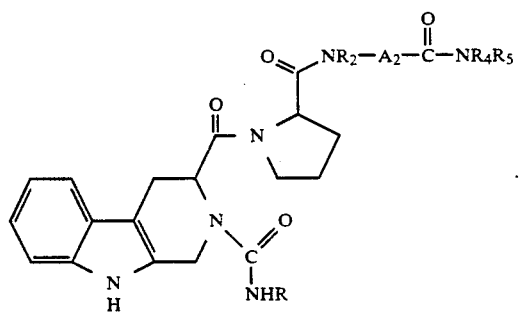

9. A compound according to claim 8 wherein

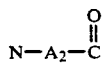

is derived from aspartic acid.

10. A compound according to claim 9 which is N-[(3R)-2-(3,4-dichlorophenylcarbamoyl)-1,2,3,4-tetrahydro-9H-pyrido[3,4-b]indol-3-yl]carbonyl-L-prolyl-L-aspartic acid amide or a pharmaceutically acceptable salt thereof.

11. A compound of claim 1 which is:

N-[(3R)-2-(3-methylphenylcarbamoyl)-1,2,3,4-tetrahydro-9H-pyrido[3,4-b]indole-3-carboxyl]-L-leucyl-L-aspartic acid amide;

N-[(3S)-2-(3-methylphenylcarbamoyl)-1,2,3,4-tetrahydro-9H-pyrido[3,4-b]indole-3-carboxyl]-L-leucyl-L-aspartic acid amide;

N-[(3R)-2-phenylcarbamoyl-1,2,3,4-tetrahydro-9H-pyrido[3,4-b]indole-3-carboxyl]-L-leucyl-L-aspartic acid amide;

N-[(3R)-2-(3-methylphenylcarbamoyl)-1,2,3,4-tetrahydro-9H-pyrido[3,4-b]indole-3-carboxyl]-D-leucyl-D-aspartic acid amide;

N-[(3S)-2-(3-methylphenylcarbamoyl)-1,2,3,4-tetrahydro-9H-pyrido[3,4-b]indole-3-carboxyl]-D-leucyl-D-aspartic acid amide;

N-[(3R)-2-(3-methylphenylcarbamoyl)-1,2,3,4-tetrahydro-9H-pyrido[3,4-b]indole-3-carboxyl]-L-leucyl-D-aspartic acid amide;

N-[(3S)-2-(3-methylphenylcarbamoyl)-1,2,3,4-tetrahydro-9H-pyrido[3,4-b]indole-3-carboxyl]-D-leucyl-L-aspartic acid amide;

N-[(3R)-2-(3-methylphenylcarbamoyl)-1,2,3,4-tetrahydro-9H-pyrido[3,4-b]indole-3-carboxyl]N'-methyl--L-leucyl-L-aspartic acid amide;

N-[(3R)-2-(4-chlorophenylcarbamoyl)-1,2,3,4-tetrahydro-9H-pyrido[3,4-b]indole-3-carboxyl]-L-leucyl-L-aspartic acid amide;

N-[(3R)-2-(3-methylphenylcarbamoyl)-1,2,3,4-tetrahydro-9H-pyrido[3,4-b]indole-3-carboxyl]-D-leucyl-L-aspartic acid amide;

N-[(3R)-2-(3,5-dichlorophenylcarbamoyl)-1,2,3,4-tetrahydro-9H-pyrido[3,4-b]indole-3-carboxyl]-L-leucyl-L-aspartic acid amide;

N-[(3R)-2-(3,5-dimethylphenylcarbamoyl)-1,2,3,4-tetrahydro-9H-pyrido[3,4-b]indole-3-carboxyl]-L-leucyl-L-aspartic acid amide;

N-[(3R)-2-(3-methoxyphenylcarbamoyl)-1,2,3,4-tetrahydro-9H-pyrido[3,4-b]indole-3-carboxyl]-L-leucyl-L-aspartic acid amide;

N-[(3R)-2-(2-naphthylcarbamoyl)-1,2,3,4-tetrahydro-9H-pyrido[3,4-b]indole-3-carboxyl]-L-leucyl-L-aspartic acid amide;

N-[(3R)-2-(3-trifluoromethylphenylcarbamoyl)-1,2,3,4-tetrahydro-9H-pyrido[3,4-b]indole-3-carboxyl]-L-leucyl-L-aspartic acid amide;

N-[(3R)-2-(3-fluorophenylcarbamoyl)-1,2,3,4-tetrahydro-9H-pyrido[3,4-b]indole-3-carboxyl]-L-leucyl-L-aspartic acid amide;

N-[(3R)-2-(3,4-dichlorophenylcarbamoyl)-1,2,3,4-tetrahydro-9H-pyrido[3,4-b]indole-3-carboxyl]-L-leucyl-L-aspartic acid amide;

N-[(3R)-2-(1-naphthylcarbamoyl)-1,2,3,4-tetrahydro-9H-pyrido[3,4-b]indole-3-carboxyl]-L-leucyl-L-aspartic acid amide;

N-[(3S)-2-(3,4-dichlorophenylcarbamoyl)-1,2,3,4-tetrahydro-9H-pyrido[3,4-b]indole-3-carboxyl]-D-leucyl-D-aspartic acid amide;

N-[2-(3-methylphenylcarbamoyl)-1,2,3,4-tetrahydro-9H-pyrido[3,4-b]indole-3-carboxyl]-L-leucyl-L-aspartic acid amide;

N-[(3R)-2-(2,3-dichlorophenylcarbamoyl)-1,2,3,4-tetrahydro-9H-pyrido[3,4-b]indole-3-yl]-carbonyl-L-leucyl-L-aspartic acid amide;

N-[(3R)-2-(4-methoxyphenylcarbamoyl)-1,2,3,4-tetrahydro-9H-pyrido[3,4-b]indole-3-yl]-carbonyl-L-leucyl-L-aspartic acid amide; or N-[(3R)-2-(3-methylphenylcarbamoyl)-1,2,3,4-tetrahydro-9H-pyrido[3,4-b]indole-3-yl]-carbonyl-L-leucyl-D-aspartic acid amide; or a pharmaceutically acceptable salt thereof.

12. A compound of claim 1 which is:

N-[(3R)-2-(3-methylphenylcarbamoyl)-1,2,3,4-tetrahydro-9H-pyrido[3,4-b]indole-3-carboxyl]-L-prolyl-L-aspartic acid amide;

N-[(3S)-2-(3-methylphenylcarbamoyl)-1,2,3,4-tetrahydro-9H-pyrido[3,4-b]indole-3-carboxyl]-D-prolyl-D-aspartic acid amide;

N-[(3S)-2-(3,4-dichlorophenylcarbamoyl)-1,2,3,4-tetrahydro-9H-pyrido[3,4-b]indole-3-carboxyl]-D-prolyl-D-aspartic acid amide; or N-[(3R)-2-(3,4-dichlorophenylcarbamoyl)-1,2,3,4-tetrahydro-9H-pyrido[3,4-b]indole-3-yl]-carbonyl-L-prolyl-L-aspartic acid amide; or a pharmaceutically acceptable salt thereof.

13. A compound of claim 1 which is:

N-[(3R)-2-(3-methylphenylcarbamoyl)-1,2,3,4-tetrahydro-9H-pyrido[3,4-b]indole-3-carboxyl]-L-leucyl-L-phenylalanine amide;

N-[(3R)-2-(3-methylphenylcarbamoyl)-1,2,3,4-tetrahydro-9H-pyrido[3,4-b]indole-3-carboxyl]-L-leucyl-L-asparagine;

N-[(3R)-2-(3-methylphenylcarbamoyl)-1,2,3,4-tetrahydro-9H-pyrido[3,4-b]indole-3-carboxyl]-L-leucyl-L-glutamic acid amide;

N-[(3R)-2-(3,4-dichlorophenylcarbamoyl)-1,2,3,4-tetrahydro-9H-pyrido[3,4-b]indole-3-carboxyl]-L-leucyl-L-glutamic acid amide;

N-[(3R)-2-(3,4-dichlorophenylcarbamoyl)-1,2,3,4-tetrahydro-9H-pyrido[3,4-b]indole-3-yl]-carbonyl-L-leucyl-$\beta$-alanine;

N-[(3R)-2-(3,4-dichlorophenylcarbamoyl)-1,2,3,4-tetrahydro-9H-pyrido[3,4-b]indole-3-yl]-carbonyl-L-glycinamide;

N-[(3S)-2-(3-methylphenylcarbamoyl)-1,2,3,4-tetrahydro-9H-pyrido[3,4-b]indole-3-carboxyl]-D-leucyl-D-aspartic acid amide;

N-[(3R)-2-(3-methylphenylcarbamoyl)-1,2,3,4-tetrahydro-9H-pyrido[3,4-b]indole-3-yl]-carbonyl-L-leucyl--L--O-benzyl-serine;

N-[(3R)-2-(2,3-dichlorophenylcarbamoyl)-1,2,3,4-tetrahydro-9H-pyrido[3,4-b]indole-3-yl]-carbonyl-L-leucyl-glycinamide;

N-[(3R)-2-(2,3-dichlorophenylcarbamoyl)-1,2,3,4-tetrahydro-9H-pyrido[3,4-b]indole-3-yl]-carbonyl-L-leucyl-$\beta$-alanine;

N-[(3R)-2-(3-methylphenylcarbamoyl)-1,2,3,4-tetrahydro-9H-pyrido[3,4-b]indole-3-yl]-carbonyl-L-leucyl-glycinamide; or N-[(3R)-2-(3-methylphenylcarbamoyl)-1,2,3,4-tetrahydro-9H-pyrido[3,4-b]indole-3-yl]-carbonyl-L-leucyl-$\beta$alanine; or a pharmaceutically acceptable salt thereof.

14. A compound of claim 1 which is:

N-[(3R)-2-(3-methylphenylcarbamoyl)-1,2,3,4-tetrahydro-9H-pyido[3,4-b]indole-3-carboxyl]glycyl-L-aspartic acid amide;

N-[(3R)-2-(3-methylphenylcarbamoyl)-1,2,3,4-tetrahydro-9H-pyrido[3,4-b]indole-3-carboxyl]-L-alanyl-L-aspartic acid amide;

N-[(3R)-2-(3-methylphenylcarbamoyl)-1,2,3,4-tetrahydro-9H-pyrido[3,4-b]indole-3-carboxyl]-O-benzyl-L-seryl-L-aspartic acid amide;

N-[(3R)-2-(3,4-dichlorophenylcarbamoyl)-1,2,3,4-tetrahydro-9H-pyrido[3,4-b]indole-3-yl]-carbonyl-L-isoleucyl-L-aspartic acid amide; or N-[(3R)-2-(3-methylphenylcarbamoyl)-1,2,3,4-tetrahydro-9H-pyrido[3,4-b]indole-3-yl]-carbonyl-L-isoleucyl-L-aspartic acid amide; or a pharmaceutically acceptable salt thereof.

15. A compound of claim 1 which is

N-[(3R)-2benzoyl-1,2,3,4-tetrahydro-9H-pyrido[3,4-b]indole-3-carboxyl]-L-leucyl-L-aspartic acid amide;

N-[(3R)-2-(2-naphthoyl)-1,2,3,4-tetrahydro-9H-pyrido[3,4-b]indole-3-carboxyl]-L-leucyl-L-aspartic acid amide;

N-[(3R)-2-(1-naphthoyl)-1,2,3,4-tetrahydro-9H-pyrido[3,4-b]indole-3-carboxyl]-L-leucyl-L-aspartic acid amide-$\beta$-benzyl ester;

N-[(3R)-2-(2-naphthoyl)-1,2,3,4-tetrahydro-9H-pyrido[3,4-b]indole-3-carboxyl]-L-leucyl-L-aspartic acid amide-$\beta$-benzyl ester;

N-[(3R)-2-(3-methylbenzoyl)-1,2,3,4-tetrahydro-9H-pyrido[3,4-b]indole-3-carboxyl]-L-leucyl-L-aspartic acid amide; or N-[(3R)-2(3,4-dichlorobenzoyl)-1,2,3,4-tetrahydro-9H-pyrido[3,4-b]indole-3-carboxyl]-L-leucyl-L-aspartic acid amide; or a pharmaceutically acceptable salt thereof.

16. A compound of claim 1 which is:

N-[(3R)-1,2,3,4-tetrahydro-9H-pyrido[3,4-b]indole-3-carboxyl]-L-leucyl-L-aspartic acid amide;

N-[(3S)-1,2,3,4-tetrahydro-9H-pyrido[3,4-b]indole-3-carboxyl]-L-leucyl-L-aspartic acid amide; or N-[(3R)-1,2,3,4-tetrahydro-9H-pyrido[3,4-b]indole-3-carboxyl]-L-leucyl-L-aspartic acid amide-$\beta$-benzyl ester; or a pharmaceutically acceptable salt thereof.

17. A pharmaceutical composition comprising a therapeutically-effective amount for antagonism of the function of cholecystokinins or gastrin in a mammal or a compound according to claim 1 and a pharmaceutically acceptable carrier.

18. The pharmaceutically acceptable composition of claim 17 further comprising an adjuvant.

19. A method of treating a mammal for cholecystokinin or gastrin-related disorders of the gastrointestinal, central nervous or appetite regulatory systems which comprises administering to said mammal a therapeutically effective amount of a compound, according to claim 1.

20. A method of treating a mammal for cholecystokinin or gastrin-related disorders of the gastrointestinal, central nervous or appetite regulatory systems which comprises administering to said mammal a therapeutically effective amount of the composition according to claim 18.

* * * * *